(12) United States Patent
Rigas

(10) Patent No.: US 8,236,820 B2
(45) Date of Patent: Aug. 7, 2012

(54) ANTI-INFLAMMATORY COMPOUNDS AND USES THEREOF

(76) Inventor: Basil Rigas, Setauket, NY (US)

( * ) Notice: Subject to any disclaimer, the term of this patent is extended or adjusted under 35 U.S.C. 154(b) by 837 days.

(21) Appl. No.: 12/189,500

(22) Filed: Aug. 11, 2008

(65) Prior Publication Data

US 2009/0099137 A1 Apr. 16, 2009

Related U.S. Application Data

(60) Provisional application No. 60/955,258, filed on Aug. 10, 2007, provisional application No. 60/989,584, filed on Nov. 21, 2007.

(51) Int. Cl.
*A01N 47/00* (2006.01)
(52) U.S. Cl. ........ 514/320; 514/107; 514/110; 514/124; 558/160; 558/196; 558/197; 558/198; 558/86
(58) Field of Classification Search .......... 514/107, 514/110, 124, 320; 558/160, 196, 197, 198, 558/86
See application file for complete search history.

(56) References Cited

U.S. PATENT DOCUMENTS

| | | | |
|---|---|---|---|
| 3,396,193 A | | 8/1968 | Freedman et al. |
| 4,006,204 A | | 2/1977 | Rajadhyaksha et al. |
| 6,040,341 A | | 3/2000 | Del Soldato et al. |
| 2003/0060465 A1* | | 3/2003 | Jilani .................... 514/233.5 |
| 2004/0102517 A1 | | 5/2004 | Chen et al. |
| 2005/0239725 A1* | | 10/2005 | Gallop et al. .................... 514/35 |

FOREIGN PATENT DOCUMENTS

| | | |
|---|---|---|
| DE | 201 10 355 U1 | 10/2001 |
| EP | 0 332 129 A2 | 9/1989 |
| EP | 0 693 494 A1 | 1/1996 |
| WO | WO 00/44705 A | 8/2000 |
| WO | WO 02/092072 A2 | 11/2002 |
| WO | WO 03/013499 A | 2/2003 |
| WO | WO 03/084550 A | 10/2003 |
| WO | WO 2005/065361 A2 | 7/2005 |
| WO | WO 2008/078965 A1 | 7/2008 |

OTHER PUBLICATIONS (Vippagunta, et al. Advanced Drug Delivery Reviews, 48, 2001, p. 18).*
Wolff, Manfred E., Ed. Burger's Medicinal Chemistry and Drug Discovery—Fifth Edition, New York: John Wiley & Sons,1996, vol. 1, pp. 974-976).*
STN:Accession No. 1995:999863.*
Banazczyk et al "Propofol phosphate, a water soluble propofol prodrug: in vivo evaluation", Anesth., Analg., 2002;95:1285-92.*
Asakawa, H. et al., Chem. Pharm. Bull. 27(2), p. 522-527 (1979).
Heaney, F. et al., J. Chem. Soc. Perkin Trans. 2 vol. 2, p. 547-560 (1998).
Jubert, C. et al., J. Org. Chem., vol. 57, p. 5425-31 (1992).
Kashfi, K. et al., J. Pharm. Exp. Ther. 303(3), p. 1273-1282 (2002).
Suh, Y et al., J. Organomet. Chem., vol. 684, p. 20-36 (2003).

* cited by examiner

*Primary Examiner* — Brandon Fetterolf
*Assistant Examiner* — Jean Cornet
(74) *Attorney, Agent, or Firm* — Chalin A. Smith; Smith Patent Consulting, LLC

(57) ABSTRACT

Compounds of the general formula

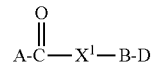

Formula (I)

are disclosed with activity towards treating diseases related to inflammation, such as cancer, neurodegenerative and cardiovascular diseases. Pharmaceutical compositions and methods of use are also described.

21 Claims, 14 Drawing Sheets

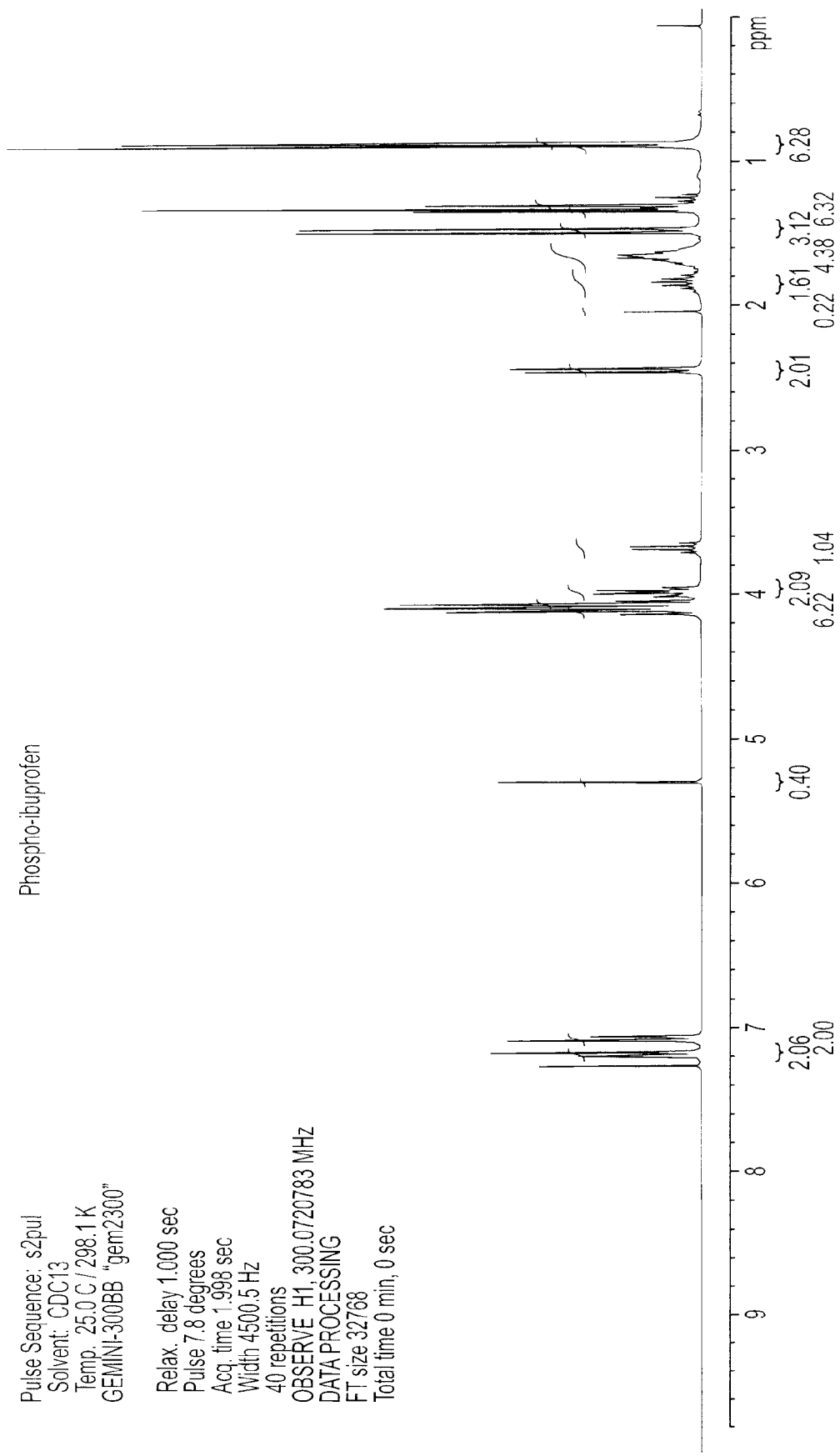

ANTI-INFLAMMATORY COMPOUNDS AND USES THEREOF

CROSS-REFERENCES TO RELATED APPLICATIONS

This application claims priority of U.S. Provisional Application Ser. No. 60/955,258, filed Aug. 10, 2007, and U.S. Provisional Application Ser. No. 60/989,584, filed Nov. 21, 2007. The contents of both provisional applications are incorporated herein by reference in their entirety.

FIELD OF THE INVENTION

The invention is directed to compounds and pharmaceutical compositions for the treatment of inflammation-related diseases, in particular cancer.

BACKGROUND OF THE INVENTION

Inflammation, a key component of the immune system, functions in both defense and pathophysiological events to maintain the homeostasis of tissues, organs and individual cells. Inflammation can be classified as either acute or chronic. Acute inflammation is a short-term process characterized by the classic signs of inflammation, i.e. swelling, redness, pain, heat, and loss of function, due to infiltration of tissues by plasma and leukocytes. It occurs as long as the injurious stimulus is present and ceases once the stimulus has been removed. Chronic inflammation is a pathological condition characterized by concurrent active inflammation, tissue destruction, and attempts at repair. Chronically inflamed tissue is characterized by the infiltration of mononuclear immune cells (monocytes, macrophages, lymphocytes, and plasma cells), tissue destruction, and attempts at healing, which include angiogenesis and fibrosis.

Without inflammation, wounds and infections would not be able to heal and progressive destruction of the tissue would threaten the survival of the organism. Unchecked inflammation, on the other hand, can lead to a host of diseases, such as hay fever, atherosclerosis and other cardiovascular diseases, neurodegenerative diseases such as Alzheimer's, cancer and rheumatoid arthritis. For these reasons, inflammation is tightly regulated by the body.

Inflammation is controlled by more than 400 genes. The pro-inflammatory genotype, which appears dominant, increases our vulnerability to, and intensity of, inflammatory reactions, which underlie chronic inflammatory diseases, especially in old age. (Ferencik et al., Inflammation—a lifelong companion. Folia Microbiol (Praha). 2007; 52:159-73). Although joint diseases have long been the prototypical inflammatory diseases, cardiovascular diseases, neurodegenerative diseases, autoimmune diseases, and cancer are now appreciated as having inflammation as a unifying component of their pathogenesis.

Alzheimer's disease (AD) includes inflammatory processes in the senile plaques and surrounding glia, with increased expression of acute phase proteins such as C-reactive protein (CRP) and IL-6. Increased IL-6 expression during normal brain aging suggests a link of age-related inflammation to the onset of AD during aging. Blood levels of CRP and IL-6 are also associated with higher risk of Alzheimer's disease and cognitive decline during aging (Finch and Morgan, Systemic inflammation, infection, ApoE alleles, and Alzheimer disease: a position paper. Curr Alzheimer Res. 2007; 4:185-9).

Inflammation plays a crucial role in all steps characterizing the atherosclerotic process. Circulating CRP (C-reactive protein) levels have emerged as a powerful independent determinant of cardiovascular events. Hypertension is closely linked to inflammation. Experimental data and results from cross-sectional studies in humans strongly support this notion (Virdis et al., C-reactive protein and hypertension: is there a causal relationship? Curr Pharm Des. 2007; 13:1693-8). In cancer, chronic inflammation often acts as a tumor promoter, resulting in aggressive cancerous growth and spread. Many of the same inflammatory factors that promote tumor growth also are responsible for cancer cachexia/anorexia, pain, debilitation, and shortened survival. A compelling case has been made even for attacking inflammation at initial diagnosis to improving patient quality of life and survival. Serum levels of CRP correlate with poor prognosis in cancer patients (MacDonald N. Cancer cachexia and targeting chronic inflammation: a unified approach to cancer treatment and palliative/supportive care. J Support Oncol. 2007; 5:157-62).

Nonsteroidal anti-inflammatory drugs (NSAIDS) are the most widely used anti-inflammatory compounds, with aspirin, the prototypical NSAID, still being one of the oldest and most extensively used medication in the world (Stanley P, Hegedus R. Aspirin—the first hundred years. Biologist (London) 2000; 47:269-71; Rinsema T J. One hundred years of aspirin. Med Hist 1999; 43:502-7). NSAIDs have a significant antineoplastic effect, which should be viewed, at least in part, in the context of the increasingly appreciated role of inflammation in cancer. Aspirin is formally documented to be a chemopreventive agent against colon cancer [3,4]. For other NSAIDS, the evidence on their antineoplastic properties is quite strong but still it is based mainly on epidemiological studies (Baron J A. What now for aspirin and cancer prevention? J Natl Cancer Inst 2004; 96:4-5; Jacobs E J, Rodriguez C, Mondul A M, Connell C J, Henley S J, Calle E E, et al. A large cohort study of aspirin and other nonsteroidal anti-inflammatory drugs and prostate cancer incidence. J Natl Cancer Inst 2005; 97:975-80; Thun M J, Henley S J, Gansler T Inflammation and cancer: an epidemiological perspective. Novartis Foundation symposium 2004; 256:6-21; discussion 2-8, 49-52, 266-9). For example, a recent meta-analysis of 91 epidemiological studies showed a significant exponential decline with increasing intake of NSAIDs in the risk for 7-10 malignancies including the four major types: colon, breast, lung, and prostate cancer (Harris R E, Beebe-Donk J, Doss H, Burr Doss D. Aspirin, ibuprofen, and other non-steroidal anti-inflammatory drugs in cancer prevention: a critical review of non-selective COX-2 blockade (review). Oncology reports 2005; 13:559-83; Ratliff T L. Aspirin, ibuprofen, and other non-steroidal anti-inflammatory drugs in cancer prevention: a critical review of non-selective COX-2 blockade (review). The Journal of urology 2005; 174:787-8).

NSAIDs prevent cancer likely through pleiotropic effects (reviewed in Rayyan Y, Williams J, Rigas B. The role of NSAIDs in the prevention of colon cancer. Cancer Invest 2002; 20:1002-11; Shiff S J, Rigas B. Aspirin for cancer. Nat Med 1999; 5:1348-9.). It is, however, clear that conventional NSAIDs do not meet two important criteria for their wide application as chemopreventive agents against cancer, i.e. safety and high efficacy, as NSAIDs are associated with a considerable number of side effects, and their efficacy is rather limited, not exceeding 50% (Rayyan Y, Williams J, Rigas B. The role of NSAIDs in the prevention of colon cancer. Cancer Invest 2002; 20:1002-11). Thus there is a need to develop compounds with improved efficacy and safety profiles for the treatment of various diseases related to inflammation.

SUMMARY OF THE INVENTION

The present invention provides such novel therapeutics including a novel group of NSAID derivatives and method of using them in the prevention and treatment of diseases, especially cancers.

In a first aspect, the present invention provides compounds of general Formula I:

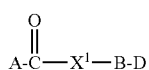

Formula (I)

or an enantiomer, racemate, diastereomer, or tautomer thereof, or a prodrug, salt, hydrate or ester thereof;
wherein $X^1$ is selected from the group consisting of —O— —S— and —NH—;
wherein B is an optionally substituted aliphatic, alicyclic, heteroaliphatic, heterocyclic, aromatic, or heteroaromatic group,
wherein B is optionally substituted with one or more $X^2$ which is independently selected from the group consisting of hydrogen, halogen, hydroxyl, alkoxyl or —CN; an optionally substituted aliphatic, alicyclic, heteroaliphatic, heterocyclic, aromatic, heteroaromatic moiety; —$OR^R$, —$S(=O)_nR^d$, —$NR^bR^c$, —$C(=O)R^a$ and —$C(=O)OR^a$; wherein n is 0-2, $R^R$ is an optionally substituted aliphatic, alicyclic, heteroaliphatic, heterocyclic, aryl or aralkyl, heteroaromatic group or acyl moiety;
$R^a$, for each occurrence, is independently selected from the group consisting of hydrogen and an optionally substituted aliphatic, alicyclic, heteroaliphatic, heterocyclic, aromatic, or a heteroaromatic moiety;
$R^b$ and $R^cC$, for each occurrence, are independently selected from the group consisting of hydrogen; hydroxy; $SO_2R^d$; and aliphatic, alicyclic, heteroaliphatic, heterocyclic, aromatic, heteroaromatic or an acyl moiety;
$R^d$, for each occurrence, is independently selected from the group consisting of hydrogen; —$N(R^e)_2$; aliphatic, aryl and heteroaryl; and
$R^e$, for each occurrence, is independently hydrogen or an aliphatic group;
wherein A is an optionally substituted aliphatic, alicyclic, heteroaliphatic, heterocyclic, aromatic, or heteroaromatic group such as but not limited to those moieties described in further detail herein below;
wherein D is hydroxyl; halide; tosylate; phosphate ester (—O—$P(OR^f)_3$) or a phosphite ester (—O—$P(OR^g)_2$), —$OSO_2NR_xR_y$, where $R_x$ and $R_y$ are independently hydrogen, or a substituted or unsubstituted aliphatic, alicyclic, heteroaliphatic, heterocyclic, aryl or aralkyl, heteroaromatic or acyl moiety; —O—$C_6H_4OC(=O)CH_3$; an alkoxy moiety; or an acyl moiety, provided that at least one $R^f$ is not an H, and at least one $R^g$ is not an H, and provided that if B is

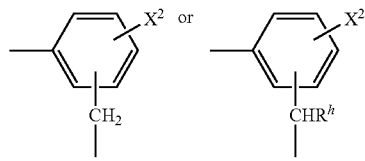

where $R^h$ is aryl, aralkyl, alkyl, alkenyl or alkynyl, then D is a phosphate ester (—O—$P(O)(OR^f)_2$) or a phosphite ester (—O—$P(OR^g)_2$), preferably, $R^f$ and $R^g$ is independently each an H, alkyl, alkenyl, alkynyl, aryl or an aralkyl group, which may in turn be substituted or unsubstituted.

In one embodiment, the present invention relates to mono-, di- or tri-esters of phosphoric acid or phosphorous acid of aspirin, containing alkyl, alkenyl, aryl, benzyl or cyclic groups and their derivatives, and the use thereof for cancer treatment and prevention. A series of novel aspirin derivatives, in particular 2-acetoxy-benzoic acid 4-(diethoxy-phosphoryloxymethyl)-phenyl ester, and 2-acetoxy-benzoic acid 3-(diethoxy-phosphoryloxymethyl)-phenyl ester, provisionally named phosphoaspirins, and determined these compounds have anticancer activities both in vitro and in vivo. Phosphoaspirin inhibited the growth of HT-29 human colon adenocarcinoma cells ($IC_{50}$=276.6±12.3 µM (mean±SEM) through a combined antiproliferative and mainly proapoptotic effect. While not willing to be bound by any theory on mechanism, applicant believes that phosphoaspirin achieves this effect by modulating cell kinetics; the proliferation index of cancer cells was reduced by 18.13% compared to controls ($p<0.001$) and the apoptosis index was increased by 94.6% ($p<0.003$). No apparent toxicity was shown by phosphoaspirin.

Preferably, compound of formula I is selected from the following: Diethyl 4-(2-acetoxylbenzoyloxy)benzyl phosphate, 2-acetoxy-benzoic acid 4-(diethoxy-phosphoryloxymethyl)-phenyl ester, 2-acetoxy-benzoic acid 3-(diethoxy-phosphoryloxymethyl)-phenyl ester, and phospho-sulindac I, phospho-sulindac II, phosphoflurbiprofen, phosphoibuprofen, glycero-phosphoaspirin I, and glycero-phosphoraspirin II. The chemical structures of these compounds are provided hereinbelow.

In a further aspect, the invention is directed to a pharmaceutical composition comprising a compound of Formula I, as described generally herein, and a pharmaceutically acceptable excipient. In a specific embodiment, the composition is useful in the treatment of human and animal inflammation related diseases, including, but not limited to neoplasms, cancer, rheumatologic diseases such as rheumatoid arthritis and Sjogren's syndrome; cardiovascular diseases, such as coronary artery disease, peripheral vascular disease and hypertension; neurodegenerative diseases, such as Alzheimer's disease and its variants or cerebrovascular diseases; and autoimmune diseases for example lupus erythematosus. Such compositions can comprise one or more other pharmaceutical agents in addition to one or more compounds of the invention.

In another embodiment, the invention is directed to a method for inhibiting inflammation, in particular chronic inflammation in a subject in need thereof by administering to the subject an amount of the compound or composition of the present invention effective to inhibit inflammation. The subject may be a human patient or animal.

In yet another aspect, the present invention provides methods for treating any disorder related to undesirable inflammation comprising administering to a subject (e.g., human patient or animal) in need thereof a therapeutically effective amount of a compound of Formula I of the invention or a pharmaceutical composition comprising a compound of the invention. In a preferred embodiment, the disorder includes, but is not limited to rheumatologic diseases such as for example rheumatoid arthritis and Sjogren's syndrome; cardiovascular diseases, such as, for example, coronary artery disease, peripheral vascular disease and hypertension; neurodegenerative diseases, such as, for example, Alzheimer's disease and its variants or cerebrovascular diseases; autoimmune diseases such as for example lupus erythematosus; and other conditions characterized by chronic inflammation of organs such as for example the lung, such as chronic bronchitis or the sinuses, such as chronic sinusitis.

The compounds of the present invention may be used for the manufacture of a medicament for treatment of a disease listed above.

DETAILED DESCRIPTION OF THE INVENTION

Definitions

Figures 1, 1A:
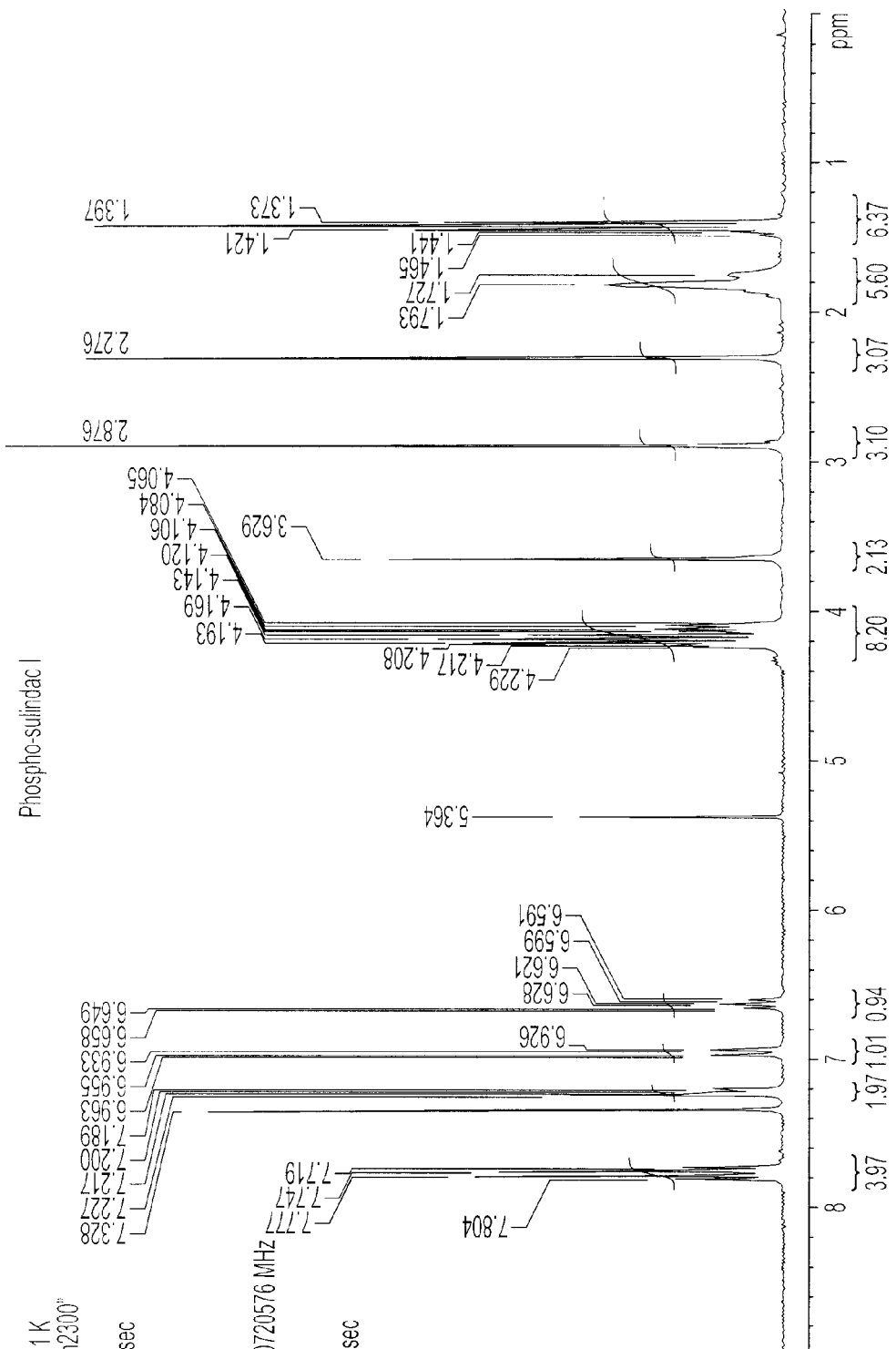
FIG. 1 is the NMR profiles of several of the compounds of the present invention.
Figures 1, 1A, 2:
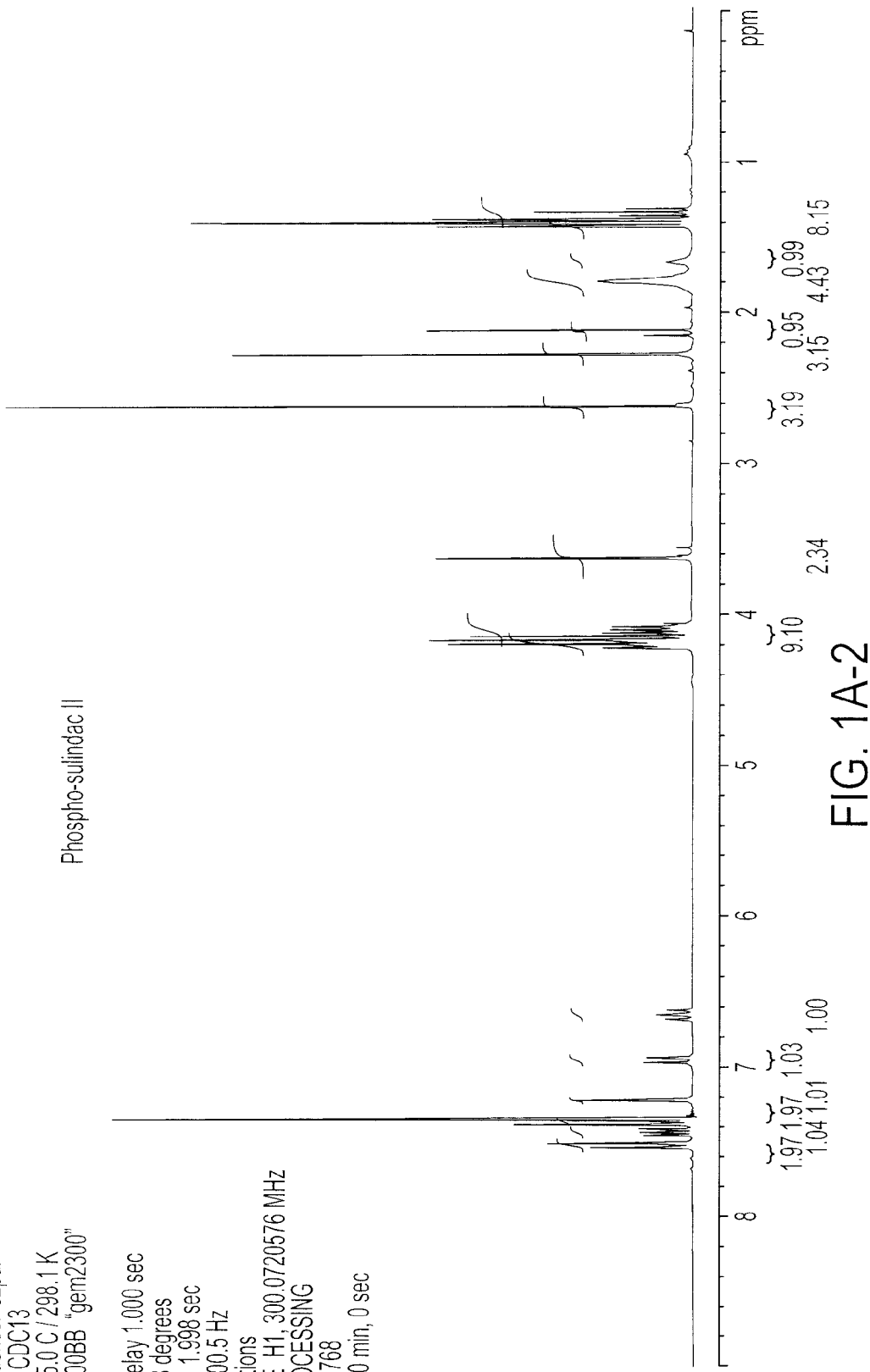
FIG. 2 shows that DFMO enhances phospho-sulindac-induced inhibition of colon cancer cell proliferation, as well as cell cycle arrest and cell death by apoptosis. A—Left panel: Cell viability was determined in HT-29 (full bars) and SW-480 (empty bars) cells after 48 h of incubation with 5 mM DFMO, 40 µM phospho-sulindac (P-S) or simultaneous combination of DFMO and P-S. Data are expressed as percentage of control cells (cells incubated only with DMSO). Values are mean±SEM of 4 independent experiments. *Significantly different from control cells ($p<0.02$, one way ANOVA test). Right panel: In this isobologram the additivity line connects the $IC_{50}$ value of each compound used alone. A and B represent two different dose pairs of each compound (their respective concentrations are shown in parentheses). The location of both A and B below the additivity line signifies synergy. B—Cell cycle progression in HT-29 cells incubated for 48 h with 5 mM DFMO, 40 µM phospho-sulindac (P-S) or simultaneous combination of DFMO and P-S. Representative profiles of the distribution of cells in G1, G2/M and S phases, out of 4 independent experiments are shown. DNA content was determined from propidium iodide (PI) fluorescence. C—Apoptosis and necrosis were determined by combined staining with annexin V and PI and determining fluorescence intensity. The percentages of apoptotic cells were determined using the dual staining with annexin V and propidium iodide and are indicated in each quadrant: left bottom quadrant, viable cells (annexin V-negative/PI-negative); right bottom quadrant, early apoptotic cells (annexin V-positive/PI-negative); right upper quadrant, late apoptotic cells (annexin V-positive/PI-positive); left upper quadrant, necrotic cells (annexin V-negative, PI-positive). These images are representative of 3 independent experiments.

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, and alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having 1-6 carbon atoms.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds, which combine the properties of aliphatic and cyclic compounds and include but are not limited to monocyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl, cyclohexyl, —CH$_2$-cyclohexyl, cyclohexenylethyl, cyclohexanylethyl, norborbyl moieties and the like, which again, may bear one or more substituents.

The term "alkoxy" or "alkyloxy", as used herein refers to a saturated (i.e., O-alkyl) or unsaturated (i.e., O-alkenyl and O-alkynyl) group attached to the parent molecular moiety through an oxygen atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, i-butoxy, sec-butoxy, tert-butoxy, neopentoxy, n-hexoxy and the like.

The term "alkylthio" or "thioalkyl" as used herein refers to a saturated (i.e., S-alkyl) or unsaturated (i.e., S-alkenyl and S-alkynyl) group attached to the parent molecular moiety through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. The term "aminoalkyl" refers to a group having the structure $NH_2R'$—, wherein R' is alkyl, as defined herein. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —$ONO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$ wherein each occurrence of $R_x$ independently includes, but is not limited to, aliphatic, alicyclic, heteroaliphatic, heterocyclic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aryl or heteroaryl substituents described above and herein may be substituted or unsubstituted. Additional examples of generally applicable substituents are illustrated by the specific embodiments shown in the Examples that are described herein.

In general, the term "aromatic moiety", as used herein, refers to a stable mono- or polycyclic, unsaturated moiety having preferably 3-14 carbon atoms, each of which may be substituted or unsubstituted. In certain embodiments, the term "aromatic moiety" refers to a planar ring having p-orbitals perpendicular to the plane of the ring at each ring atom and satisfying the Huckel rule where the number of pi electrons in the ring is (4n+2) wherein n is an integer. A mono- or polycyclic, unsaturated moiety that does not satisfy one or all of these criteria for aromaticity is defined herein as "non-aromatic", and is encompassed by the term "alicyclic."

In general, the term "heteroaromatic moiety", as used herein, refers to a stable mono- or polycyclic, unsaturated moiety having preferably 3-14 carbon atoms, each of which may be substituted or unsubstituted; and comprising at least one heteroatom selected from O, S and N within the ring (i.e., in place of a ring carbon atom). In certain embodiments, the term "heteroaromatic moiety" refers to a planar ring comprising at least one heteroatom, having p-orbitals perpendicular to the plane of the ring at each ring atom, and satisfying the Huckel rule where the number of pi electrons in the ring is (4n+2) wherein n is an integer.

It will also be appreciated that aromatic and heteroaromatic moieties, as defined herein may be attached via an alkyl or heteroalkyl moiety and thus also include -(alkyl)aromatic, -(heteroalkyl)aromatic, -(heteroalkyl)heteroaromatic, and -(heteroalkyl)heteroaromatic moieties. Thus, as used herein, the phrases "aromatic or heteroaromatic moieties" and "aromatic, heteroaromatic -(alkyl)aromatic, -(heteroalkyl)aromatic, -(heteroalkyl)heteroaromatic, and -(heteroalkyl)heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

The term "aryl", as used herein, does not differ significantly from the common meaning of the term in the art, and refers to an unsaturated cyclic moiety comprising at least one aromatic ring. In certain embodiments, "aryl" refers to a mono- or bicyclic carbocyclic ring system having one or two aromatic rings including, but not limited to, phenyl, naphthyl, tetrahydronaphthyl, indanyl, indenyl and the like.

The term "heteroaryl", as used herein, does not differ significantly from the common meaning of the term in the art, and refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)R_x$; —$S(O)_2R_x$; —$NR_x(CO)R_x$ wherein each occurrence of $R_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, alicyclic, heteroaliphatic or heterocyclic moieties, may optionally be substituted with substituents including, but not limited to aliphatic; alicyclic; heteroaliphatic; heterocyclic; aromatic; heteroaromatic; aryl; heteroaryl; alkylaryl; heteroalkylaryl; alkylheteroaryl; heteroalkyl heteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be linear or branched, and saturated or unsaturated. In certain embodiments, heteroaliphatic moieties are substituted by independent replacement of one or more of the hydrogen atoms thereon with one or more moieties including, but not limited to aliphatic; alicyclic; heteroaliphatic; heterocyclic; aromatic; heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heterocycloalkyl", "heterocycle" or "heterocyclic", as used herein, refers to compounds which combine the properties of heteroaliphatic and cyclic compounds and include, but are not limited to, saturated and unsaturated mono- or polycyclic cyclic ring systems having 5-16 atoms wherein at least one ring atom is a heteroatom selected from O, S and N (wherein the nitrogen and sulfur heteroatoms may be optionally be oxidized), wherein the ring systems are optionally substituted with one or more functional groups, as defined herein. In certain embodiments, the term "heterocycloalkyl", "heterocycle" or "heterocyclic" refers to a non-aromatic 5-, 6- or 7-membered ring or a polycyclic group wherein at least one ring atom is a heteroatom selected from O, S and N (wherein the nitrogen and sulfur heteroatoms may be optionally be oxidized), including, but not limited to, a bi- or tri-cyclic group, comprising fused six-membered rings having between one and three heteroatoms independently selected from oxygen, sulfur and nitrogen, wherein (i) each 5-membered ring has 0 to 2 double bonds, each 6-membered ring has 0 to 2 double bonds and each 7-membered ring has 0 to 3 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, heterocycles such as furanyl, thiofuranyl, pyranyl, pyrrolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, oxatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzofused derivatives thereof. In certain embodiments, a "substituted heterocycle, or heterocycloalkyl or heterocyclic" group is utilized and as used herein, refers to a heterocycle, or heterocycloalkyl or heterocyclic group, as defined above, substituted by the independent replacement of one, two or three of the hydrogen atoms thereon with but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples or generally applicable substituents are illustrated by the specific embodiments shown in the Examples, which are described herein.

Additionally, it will be appreciated that any of the alicyclic or heterocyclic moieties described above and herein may comprise an aryl or heteroaryl moiety fused thereto. Additional examples of generally applicable substituents are illustrated by the specific embodiments shown in the Examples that are described herein.

The terms "halo" "halide" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino", as used herein, refers to a primary ($-NH_2$), secondary ($-NHR_x$), tertiary ($-NR_xR_y$) or quaternary ($-N^+R_xR_yR_z$) amine, where $R_x$, $R_y$ and $R_z$ are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "acyl", as used herein, refers to a group having the general formula $-C(=O)R$, where R is an aliphatic, alicyclic, heteroaliphatic, heterocyclic, aromatic or heteroaromatic moiety, as defined herein.

The term "sulfonamido", as used herein, refers to a group of the general formula $-SO_2NR_xR_y$, where $R_x$ and $R_y$ are independently hydrogen, or an aliphatic, alicyclic, heteroaliphatic, heterocyclic, aromatic, heteroaromatic or acyl moiety, as defined herein.

The term "benzamido", as used herein, refers to a group of the general formula $PhCONR_x-$, where $R_x$ is hydrogen, or an aliphatic, alicyclic, heteroaliphatic, heterocyclic, aromatic, heteroaromatic or acyl moiety, as defined herein.

The term "$C_{1-6}$alkylidene", as used herein, refers to a substituted or unsubstituted, linear or branched saturated divalent radical consisting solely of carbon and hydrogen atoms, having from one to six carbon atoms, having a free valence "-" at both ends of the chain.

The term "$C_{2-6}$alkenylidene", as used herein, refers to a substituted or unsubstituted, linear or branched unsaturated divalent radical consisting solely of carbon and hydrogen atoms, having from two to six carbon atoms, having a free valence "-" at both ends of the radical, and wherein the unsaturation is present only as double bonds and wherein a double bond can exist between the first carbon of the chain and the rest of the molecule.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heterocyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aromatic", "heteroaromatic", "aryl", "heteroaryl" and the like encompass both substituted and unsubstituted groups.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains at least one additional moiety, which is susceptible to removal in vivo yielding the parent molecule as the pharmacologically active species. An example of a pro-drug is an ester, which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

The present invention discloses compounds and pharmaceutical compositions thereof that possess anti-inflammatory activities.

The compounds of the invention include compounds of the general formula (I) as defined below:

Formula (I)

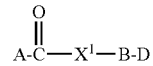

or a stereoisomer such as an enantiomer or a diastereomer or a racemate, or a tautomer thereof, or a prodrug, salt, hydrate or ester thereof;

wherein $X^1$ is selected from the group consisting of $-O-$, $-S-$, and $-NH-$;

wherein B is an optionally substituted aliphatic, alicyclic, heteroaliphatic, heterocyclic, aryl, aralkyl or a heteroaromatic group, and wherein B is optionally substituted by one or more substituents $X^2$ which is independently selected from the group consisting of hydrogen, halogen, hydroxyl, $-NO_2$, $-ONO_2$, $-CN$; an optionally substituted aliphatic, alicyclic, heteroaliphatic, heterocyclic, aromatic, heteroaromatic moiety; $-ORR^R$, $-S(=O)_nR^d$, $-NR^bR^c$, $-C(=O)R^a$ and $-C(=O)OR^a$; wherein n is 0-2, $R^R$ is an optionally substituted aliphatic, alicyclic, heteroaliphatic, heterocyclic, aromatic, heteroaromatic or acyl moiety;

$R^a$, for each occurrence, is independently selected from the group consisting of hydrogen and an optionally substituted aliphatic, alicyclic, heteroaliphatic, heterocyclic, aromatic, or a heteroaromatic moiety;

$R^b$ and $R^cC$, for each occurrence, are independently selected from the group consisting of hydrogen; hydroxy; $SO_2R^d$; and aliphatic, alicyclic, heteroaliphatic, heterocyclic, aromatic, heteroaromatic or an acyl moiety;

$R^d$, for each occurrence, is independently selected from the group consisting of hydrogen; $-N(R^e)_2$; aliphatic, aryl and heteroaryl; and $R^e$, for each occurrence, is independently hydrogen or aliphatic;

wherein A is an optionally substituted aliphatic, alicyclic, heteroaliphatic, heterocyclic, aromatic, or heteroaromatic group such as but not limited to those moieties described in further detail herein below;

wherein D is hydroxyl; halide; tosylate; phosphate ester ($-O-P(O)(OR^f)_2$) or a phosphite ester ($-O-P(OR^g)_2$), $-OSO_2NR_xR_y$, where $R_x$ and $R_y$ are independently hydrogen, or a substituted or unsubstituted aliphatic, alicyclic, heteroaliphatic, heterocyclic, aromatic, heteroaromatic or acyl moiety; $-O-C_6H_4C(=O)CH_3$; an alkoxy moiety; or an acyl moiety, provided that at least one $R^f$ is not an H, and at least one $R^g$ is not an H, and provided that if B is

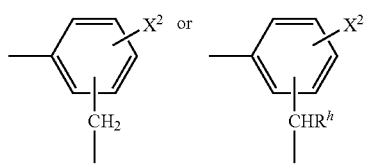

where $R^h$ is aryl, aralkyl, alkyl, alkenyl or alkynyl, then D is phosphate ester (—O—P(OR$^f$)$_3$) or a phosphite ester (—O—P(OR$^g$)$_2$), preferably, $R^f$ and $R^g$ is independently each an H, alkyl, alkenyl or an alkynyl group, which may in turn be substituted or unsubstituted.

The compounds of Formula I are not limited by the position of the substituents on an aromatic ring. For example, if B is an aromatic ring, the -D moiety may be meta, ortho or para to the A-C(=O)—X$^1$ moiety, in particular when X$^2$ is H. If one or more X$^2$ substituents are present, they may be positioned at any unoccupied position(s). Thus, any and all positional isomers of compounds of Formula I are embraced by the invention. As will be apparent from the further discussion below on synthetic methods for the compounds of the invention, the A-C(=O)—X$^1$— moiety is facilely derived from a carboxylic acid-containing reactant (A-C(=O)—OH) or an amide-containing reactant (A-C(=O)—NH), and thus the A-C(=O)—X$^1$— moiety may be referred to herein as being derived from a compound with the structure A-C(=O)—OH or A-C(=O)—NH.

In one embodiment of compounds of Formula (I) of the invention, A is

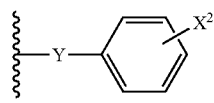

Formula (II)

wherein X$^2$ is one or more substituents as defined above, and Y is (—C—), wherein n is 0 to 4, and when n is 2 or more, Y optionally contains one or more unsaturated bonds. For example, when n=0, the optionally substituted aromatic ring is bonded to the —C(=O)—X$^1$— substituent of Formula (I). When n=1, Y is —CH$_2$—. When n=2, Y may be —CH$_2$—CH$_2$—, —CH=CH— or ethynyl radical. When n=3, Y may be —CH$_2$—CH$_2$-CH$_2$—, an allyl radical, —CH=CH—CH$_2$— or —CH$_2$—CH=CH—, or a triple bond within the radical. When n=4, the divalent radical may have any combination of saturation and unsaturation.

Among the preferred but non-limiting selections of substituent A of Formula I, in a first embodiment, A is derived from among non-steroidal anti-inflammatory drugs (NSAIDs) including but not limited to aspirin, sulindac, ibuprofen, flurbiprofen, or formula IV or an analog of either of the foregoing.

Suitable analogs of formula IV include but are not limited to derivatives with one or more fluorine atoms substituted on one or both of the benzene rings of the formula IV moiety; and compounds with one or more substitutions on the alpha carbon, such as ethyl, dimethyl, diethyl, propyl and other such aliphatic substitutions. Thus, in one embodiment, A may be

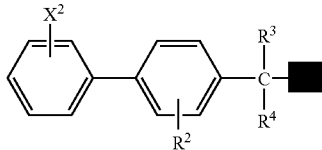

Formula (III)

wherein X$^2$ is one or more substituents as described above, R$^2$ is at least one halogen, and R$_3$ and R$_4$ are independently hydrogen or an aliphatic group. In a preferred embodiment, R$^2$ is F. In a more preferred embodiment, X$^2$ is H, R$^2$ is F (at position 3 relative to CR$^3$R$^4$) and R$^3$ and R$^4$ are H and CH$_3$, respectively.

Thus, in one preferred but non-limiting embodiment, A can be

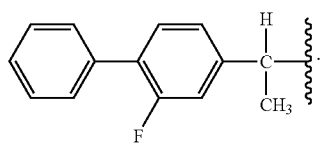

Formula (IV)

In a second embodiment, A is derived from aspirin, such as shown below:

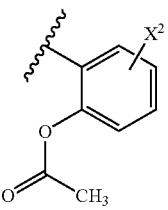

Formula (V)

where X$^2$ is one or more substituents as described above.

In a preferred but non-limiting embodiment, A is

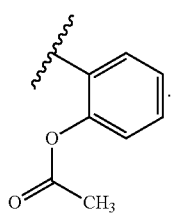

Formula (VI)

In a third embodiment, A is derived from cinnamic acid, or an analog of cinnamic acid, such as is shown below:

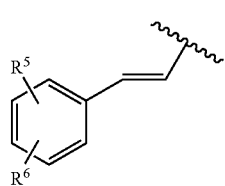

Formula (VII)

where R$^5$ and R$^6$ are independently hydrogen, —OH, alkoxy, halide, trifluoroalkyl, alpha-haloalkyl, trifluoroalkoxy, or R$^a$ as described above. Non-limiting examples of the foregoing include trifluoromethyl, alpha-fluoromethyl, 4-(anisylideneamino), 2-(hexadecyloxy), and 4-nitro-alpha-(ortho-tolyl). Examples of Formula VI from which group A in Formula I can be selected include but are not limited to 3,4-dihydroxy, o-, m- and p-hydroxy; 2,3-dihydroxy; 3,5-dihydroxy; 3,4-dimethoxy; 3-hydroxy-4-methoxy and 3,4-dimethoxy. Thus, A can be

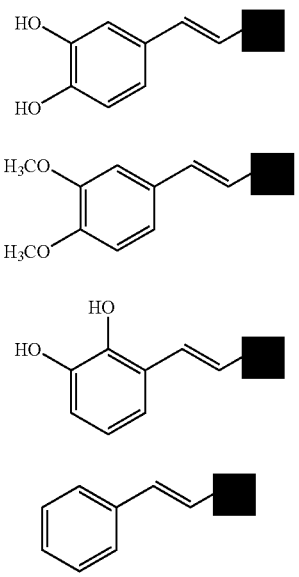

Formula (VIIa)

Formula (VIIb)

Formula (VIIc)

Formula (VIId)

In another embodiment, A is derived from phthalic acid, or an analog of phthalic acid, shown below:

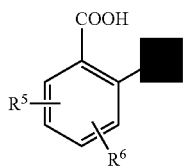

Formula (VIII)

wherein $R^5$ and $R^6$ are as described above. Examples of such A moieties include:

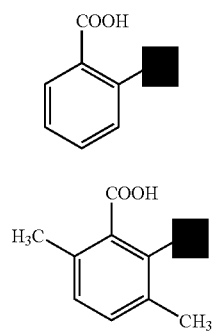

Formula (VIIIa)

Formula (VIIIb)

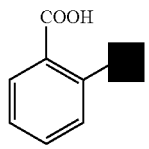

Formula (VIIIc)

In yet a further embodiment, A is a straight chain or branched aliphatic moiety, preferably 1 to 7 carbons. In compounds wherein A is an aliphatic group, $X^2$ is preferably a moiety derived from the esterification of resveratrol or an analog thereof to a carboxylic acid on the aromatic ring, i.e. $X^2$ is (—C=O)OR$^a$. Suitable analogs of resveratrol include but are not limited to the compounds described by She Q-B et al. in Oncogene, volume 22, pp 2143-2150, 2003, and in the publication by Roberti et al. in J. Med Chem, volume 46, pp 3546-3554, 2003. In one embodiment, $X^2$ is

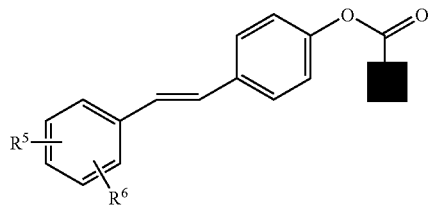

Formula (IX)

wherein $R^5$ and $R^6$ are as described above.

Non-limiting selections of $X^2$ are thus, by way of non-limiting examples,

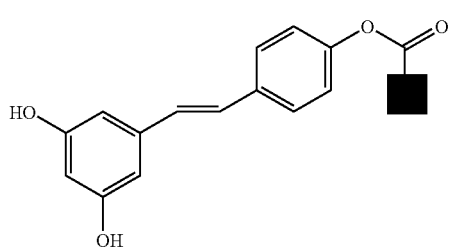

Formula (IXa)

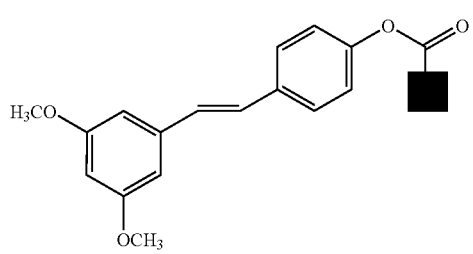

Formula (IXb)

In a preferred embodiment of the foregoing, A is methyl.

In addition to the foregoing selections of A, also embraced by the invention are compounds of Formula I wherein A is selected from the group consisting of an optionally substituted aliphatic, alicyclic, heteroaliphatic, aromatic, heterocyclic or heteroaromatic moiety.

The D substituent of Formula I is hydroxyl; halide; tosylate; phosphate ester (—O—P(O)(OR$^f$)$_2$) or a phosphite ester (—O—P(OR$^g$)$_2$), —OSO$_2$NR$_x$R$_y$, where R$_x$ and R$_y$ are independently hydrogen, or a substituted or unsubstituted aliphatic, alicyclic, heteroaliphatic, heterocyclic, aromatic, heteroaromatic or acyl moiety; —O—C$_6$H$_4$C(═O)CH$_3$; an alkoxy moiety; or an acyl moiety, provided that at least one R$^f$ is not an H, and at least one R$^g$ is not an H.

In the compounds of the present invention according to formula I, if B is

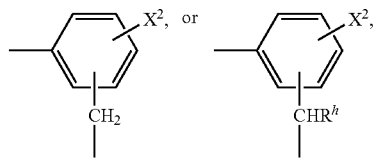

where R$^h$ is aryl, aralkyl, alkyl, alkenyl or alkynyl then D is phosphate ester (—O—P(O)(OR$^f$)$_2$) or a phosphite ester (—O—P(OR$^g$)$_2$), wherein R$^f$ and R$^g$ is independently each an H, alkyl, alkenyl or an alkynyl group, which may in turn be substituted or unsubstituted. The D substituent of Formula I is preferably a phosphate ester or a phosphite ester moiety, such as —OPO(alkyloxy)$_2$, —OPO$_2$(alkyloxy), —OP(alkyloxy)$_2$, —OPO(alkyloxy).

As noted above, in case B contains a benzene ring, the substituent containing the aforementioned D moiety, —CH$_2$-D, may be at any location on the benzene ring relative to the position of the —X$_1$—C(═O)—A substituent, i.e., meta, ortho or para thereto. The invention embraces all such positional isomers.

The selections among substituent X$^2$ are as described above. As mentioned above, in certain cases where A is an aliphatic group such as methyl, X$^2$ may be a carboxylic acid to which an alcohol or polyphenol is esterified, such as resveratrol or an analog thereof. Suitable analogs of resveratrol include but are not limited to the compounds described by She Q-B et al. in Oncogene, volume 22, pp 2143-2150, 2003, and in the publication by Roberti et al. in J. Med. Chem., volume 46, pp 3546-3554, 2003. Other preferred examples of X$^2$ include one or more —OH, —OCH$_3$, or —F, at one or more positions not occupied by the substituents containing moieties A and D. Other preferred examples of X$^2$ include —CH$_3$, and —C$_2$H$_5$.

Preferably, compound of formula I is selected from the following: 2-acetoxy-benzoic acid 4-(diethoxy-phosphoryloxymethyl)-phenyl ester, 2-acetoxy-benzoic acid 3-(diethoxy-phosphoryloxymethyl)-phenyl ester, and phospho-sulindac I, phospho-sulindac II, phosphoflurbiprofen, phosphoibuprofen, phosphoaspirin I, phosphoraspirin II, and phospho-valproic acid, as described hereinbelow.

The foregoing compounds are merely illustrative of Formula I and are not intended to be limiting.

In a further aspect, the invention is directed to a pharmaceutical composition comprising a compound of Formula I, as described generally herein, and a pharmaceutically acceptable excipient. In a specific embodiment, the composition is useful in the treatment of human and animal inflammation related diseases including but not limited to neoplasms and cancer, rheumatologic diseases such as rheumatoid arthritis and Sjogren;s syndrome; cardiovascular diseases, such as coronary artery disease, peripheral vascular disease and hypertension; neurodegenerative diseases such as Alzheimer's disease and its variants or cerebrovascular diseases; and autoimmune diseases such as lupus erythematosus; and other conditions characterized by chronic inflammation of organs such as the lung, such as chronic bronchitis or the sinuses, such as chronic sinusitis; cardiovascular diseases, for example, coronary artery disease, peripheral vascular disease and hypertension; neurodegenerative diseases, for example, Alzheimer's disease and its variants or cerebrovascular diseases; and autoimmune diseases such as lupus erythematosus; other conditions characterized by chronic inflammation of organs such as the lung, such as chronic bronchitis or the sinuses, such as chronic sinusitis; and various neoplastic and pre-neoplastic diseases, for example, benign prostatic hypertrophy, prostate cancer, colon adenomas and colon cancer, cancer of the lung, lymphomas and leukemias.

Such compositions can comprise one or more other pharmaceutical agents in addition to one or more compounds of the invention.

In another embodiment, the invention is directed to a method for inhibiting inflammation, in particular chronic inflammation in a subject in need thereof by administering to the subject an amount of the compound or composition of the present invention effective to inhibit inflammation. The subject may be a human patient or animal.

It will be appreciated that for each of the classes and subclasses described above and herein, any one or more occurrences of aliphatic or heteroaliphatic may independently be substituted or unsubstituted, cyclic or acyclic, linear or branched and any one or more occurrences of aryl, heteroaryl, cycloaliphatic, cycloheteroaliphatic may be substituted or unsubstituted.

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided. Moreover, when compounds of the invention exist in tautomeric forms, each tautomer is embraced herein.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Thus, the invention is directed to the use of the aforementioned compounds for treating inflammation-related diseases.

Thus, in a specific embodiment, the invention is directed to a method for obtaining a pharmaceutical composition, comprising formulating the compounds of the present invention into a composition comprising the compound of the present invention and a pharmaceutically acceptable carrier or excipient. The invention is further directed to uses of the compound of the present invention for manufacturing a medicament.

Compositions

As discussed above, this invention provides novel compounds that have biological properties useful for the treatment of any of a number of conditions or diseases generally characterized by abnormal inflammation, or prophylaxis in instances wherein a risk of appearance of such conditions or diseases is present. Moreover, certain compounds known in the art have been newly identified as having activity likewise useful in the prophylaxis or treatment of abnormal inflammation, and the invention is also directed to anti-inflammation compositions comprising such compounds.

Accordingly, in another aspect of the present invention, pharmaceutical compositions are provided, which comprise any one of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an approved anti-inflammation agent, or it may be any one of a number of agents undergoing approval in the Food and Drug Administration that ultimately obtain approval for the treatment of any disorder related to inflammation. Such additional therapeutic agents may also be provided to promote the targeting of the compounds of the invention to the desired site of treatment, or may increase its stability, increase its half-life, etc. It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J Pharmaceutical Sciences*, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil;

olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut (peanut), corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Compositions to deliver the agent directly to the colon—for example, pills from which the active agent is released into the colon by a pH-dependent or other mechanism ensuring exclusive or predominant colonic delivery of said compound, suppositories, enemas and other means for colonic delivery.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include but are not limited to capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms, the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include but are not limited to polymeric substances and waxes.

The present invention encompasses pharmaceutically acceptable topical formulations of inventive compounds. The term "pharmaceutically acceptable topical formulation", as used herein, means any formulation which is pharmaceutically acceptable for intradermal administration of a compound of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16$^{th}$ Edition, 1980 and 17$^{th}$ Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerin, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methyl pyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anti-inflammation agent), or they may achieve different effects (e.g., control of any adverse effects).

In certain embodiments, the pharmaceutical compositions of the present invention further comprise one or more additional therapeutically active ingredients (e.g., anti-inflammatory and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs.

In certain embodiments the compounds of the present invention can be covalently or non-covalently bound to for example polyethylene glycol or other similar molecules to make them suitable for administration to the patient either in one of the forms described above or using nanodevices. Alternatively, the compounds of the present invention can be formulated using the principles of nanoscience to optimize their therapeutic application.

Uses and Methods of Treatment

As discussed above, certain of the compounds as described herein exhibit activity generally as inhibitors of inflammation, with inflammation understood as described herein under "BACKGROUND OF THE INVENTION." Thus, in certain embodiments, compounds of the invention are useful for the treatment of any of a number of conditions or diseases in which inflammation, in particular chronic inflammation is the cause of or relates to the onset or continued occurrence of the disease or condition, such as but not limited to rheumatologic diseases such as rheumatoid arthritis and Sjogren's syndrome; cardiovascular diseases, for example, coronary artery disease, peripheral vascular disease and hypertension; neurodegenerative diseases, for example, Alzheimer's disease and its variants or cerebrovascular diseases; and autoimmune diseases such as lupus erythematosus; other conditions characterized by chronic inflammation of organs such as the lung, such as chronic bronchitis or the sinuses, such as chronic sinusitis.

Accordingly, in another aspect of the invention, methods for the treatment of inflammation-related disorders are provided comprising administering a therapeutically effective amount of a compound of Formula I to a subject in need thereof. In certain embodiments, a method for the treatment of related disorders is provided comprising administering a therapeutically effective amount of an inventive compound, or a pharmaceutical composition comprising an inventive compound to a subject in need thereof, in such amounts and for such time as is necessary to achieve the desired result.

The invention is also directed to the use of any compound of Formula (I) for the preparation of a medicament for administration to a human or animal patient in need thereof, to inhibit or block inflammation. Such compounds preferably are administered once an inflammation-related disease or an inflammatory condition that may predispose to disease has been diagnosed in the patient, optionally in combination with other anti-inflammation agents or other agents such as those that maintain therapeutic levels of the compounds within the body. Compounds of the invention also may be administered after other therapies have been tried and failed, and may be administered prophylactically.

In certain embodiments, the uses and methods of the invention involve the administration of a therapeutically effective amount of the compound or a pharmaceutically acceptable derivative thereof to a subject (including, but not limited to a human or animal, including livestock, domesticated or zoo animals) in need thereof.

It will be appreciated that the compounds and compositions, according to the method of the present invention, may be administered using any amount and any route of administration effective for the treatment of conditions or diseases in which anti-inflammation or related activities have a therapeutically useful role. Thus, the expression "effective amount" as used herein, refers to a sufficient amount of agent to inhibit inflammation and to exhibit a therapeutic effect. The exact amount required will vary from subject to subject, depending on the species, age, and general condition of the subject, the severity of the infection, the particular therapeutic agent, its mode of administration, and the like. The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the location and extent of the disease being treated. In certain embodiments, the compounds of the invention may be parenterally administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. In other embodiments, compounds of the invention may be administered orally or rectally at dosage levels of about 0.01 mg/kg to about 100 mg/kg, from about 0.05 mg/kg to about 50 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Treatment Kit

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXAMPLES

Example 1

Method of Synthesis

The following reaction scheme was followed to obtain Compound 5 (para-phosphoaspirin) of this invention shown below. Compound 5 was synthesized starting from O-Acetylsalicyloyl chloride (1) and 4-hydroxybenzaldehyde (2) in three steps, as shown below.

added diethylchlorophosphate (2.5 mL, 17.26 mmole) drop-wise, followed by DMAP (25 mg) as a solid. The reaction mixture was heated under reflux overnight. At this point the TLC showed the completion of the reaction. The reaction mixture was washed with water (2×25 mL), dried over anhydrous sodium sulfate, filtered and concentrated. The crude residue was purified by column chromatography using hexane:ethyl acetate (60:40). The pure fractions were combined and evaporated to give a solid which was triturated with hot hexane several times to give pure title compound 690 mg (25%) as a solid.

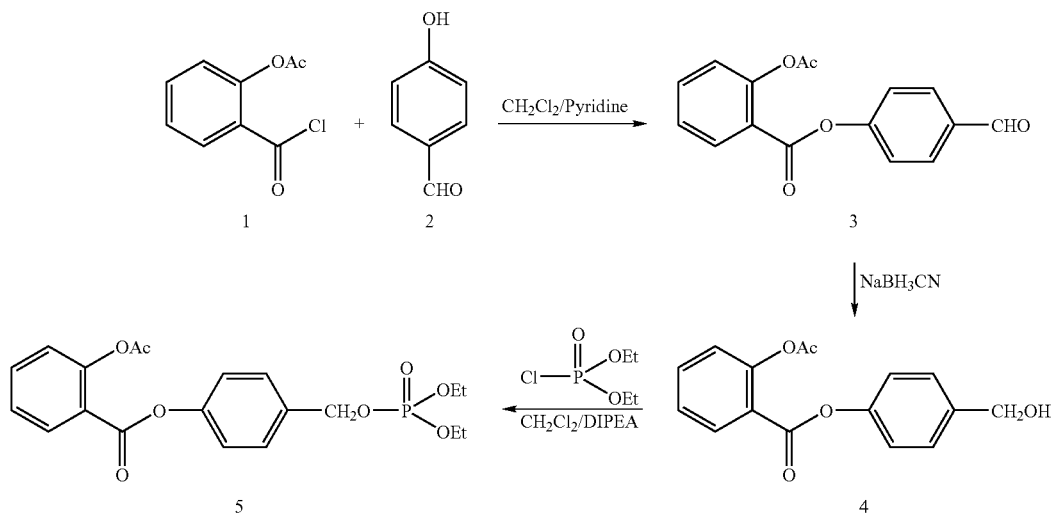

In this scheme —OEt represents $CH_3CH_2O$—.

Step 1: Preparation of Compound 3: To a pre-cooled (0° C.) solution of 4-hydroxybenzaldehyde (2, 1.04 g, 8.49 mmole) in dichloromethane (10 mL) and pyridine (4.16 mL, 50 mmole) was added O-acetylsalicyloyl chloride (1, 1.98 g, 10 mmole) in methylene chloride (10 mL) drop-wise between 0-5° C. The temperature of the reaction mixture was slowly raised to room temperature and left over night. At this point TLC of the reaction mixture showed the completion of the reaction. The reaction mixture was washed with water (25 mL), followed by 1N HCl (25 mL) and then finally with aqueous $NaHCO_3$. The organic layer was dried over anhydrous sodium sulfate, filtered and concentrated. The crude weight of the oil was 2.35 g (97%).

Step 2: Preparation of Compound 4: To a pre-cooled (0° C.) solution of compound 3 (2.3 g, 8.1 mmole) in methylene chloride (10 mL) and acetic acid (2.5 mL) was added sodium cyanoborohydride (253 mg, 4 mmole) in two portions. The temperature of the reaction was slowly raised to room temperature in 30 minutes. At this point TLC showed the completion of the reaction. The reaction mixture was washed with water (2×25 mL), followed by saturated aqueous sodium bicarbonate (25 mL) and then finally with brine. It was dried over anhydrous sodium sulfate, filtered and concentrated. The crude weight of the solid was 1.95 g (83%).

Step 3: Preparation of 2-Acetoxy-benzoic acid 4-(diethoxy-phosphoryloxymethyl)-phenyl ester (5): To a solution of alcohol (4, 1.9 g, 6.64 mmole) in methylene chloride (10 mL) and diisopropylethylamine (2.2 mL, 13.28 mmole) was To confirm purity and identity of compound 5 of this invention, TLC and $^1H$ NMR was performed. The NMR profile is shown in FIG. 1.

NSAID based compounds Non-steroidal anti-inflammatory drugs (NSAIDS) comprise a structurally and, to a large extent, functionally diverse group of compounds with nearly 50 individual compounds approved for the treatment of patients with a variety of inflammatory diseases. They all have analgesic, antipyretic and anti-inflammatory effects. Some of them, such as acetylsalicylic acid (aspirin), have been demonstrated to have an effect against inflammation-related diseases such as rheumatologic, cardiovascular, neurodegenerative and cancer, be this effect either therapeutic as, for example, in rheumatoid arthritis, or preventive as, for example, in cancer, coronary artery disease or Alzheimer's disease.

Broadly, NSAIDs can be categorized into the following chemical groups: salicylates, arylalkanoic acids (e.g. sulindac), 2-arylpropionic acids (profens), N-arylanthranilic acids (fenamic acids), pyrazolidine derivatives, oxicams, and sulphonanilides. Most of the available NSAIDs are amenable to derivatization as described herein using methods readily available and known to those ordinarily skilled in the art.

The following are examples of several derivatized NSAIDs according to certain embodiments of the invention.

The following compounds have been similarly synthesized.

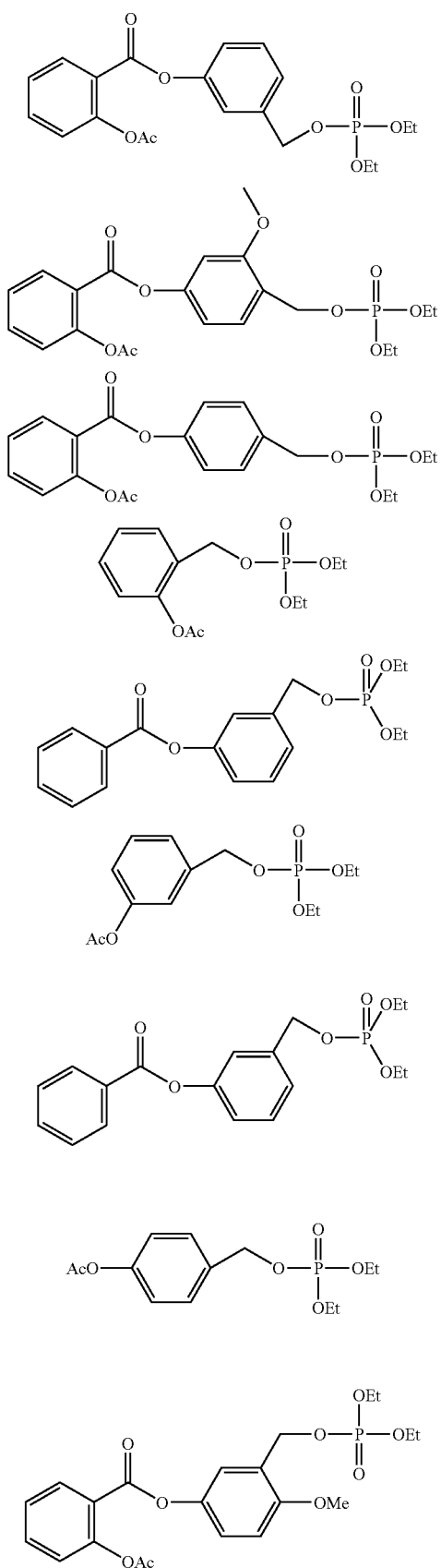
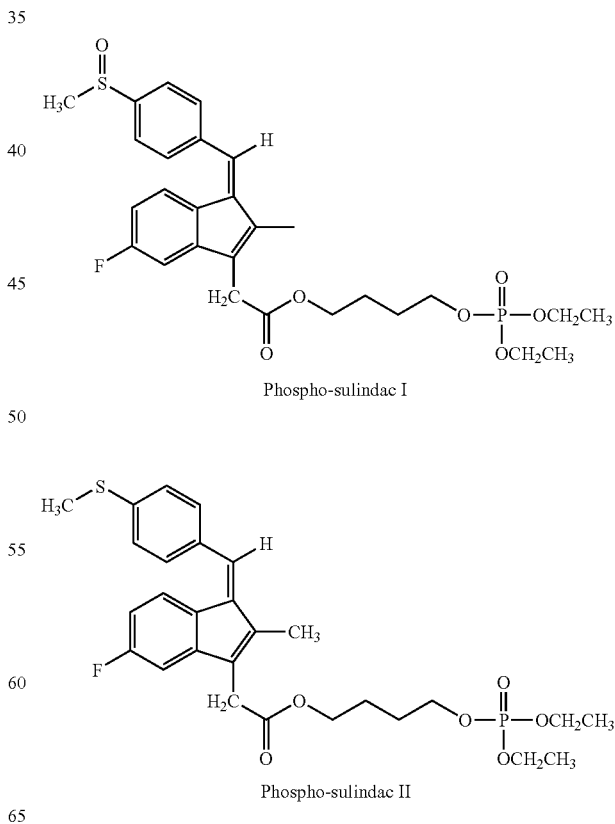
Note: -OEt represents CH₃CH₂O—.asdfad
Two derivatives of sulindac (2-[6-fluoro-2-methyl-3-[(4-methylsulfinylphenyl)methylidene]inden-1-yl]-acetic acid) were synthesized. They are referred to as phospho-sulindac I and phsphosulindac II, respectively. Their structures are:
Phospho-sulindac I
Phospho-sulindac II
and their respective ¹H-NMR profiles are shown in FIG. 1.

One derivative of ibuprofen has been synthesized and is referred to as phospho-ibuprofen. Its structure is:

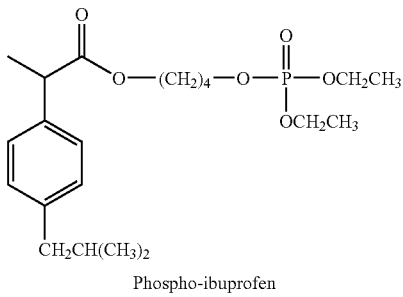

Phospho-ibuprofen and its $^1$H-NMR profile is shown in FIG. 1.

One derivative of flurbiprofen has been synthesized and is referred to as phospho-flurbiprofen. Its structure is:

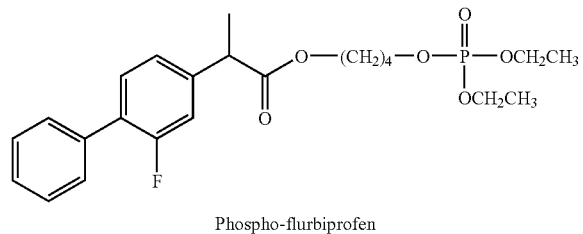

Phospho-flurbiprofen and its $^1$H-NMR profile is shown in FIG. 1.

Two derivatives of aspirin were synthesized. They are referred to as glycero-phospho-aspirin I and glycero-phospho-aspirin II, respectively. Their structures are shown below, and their respective $^1$H-NMR profiles are shown in FIG. 1.

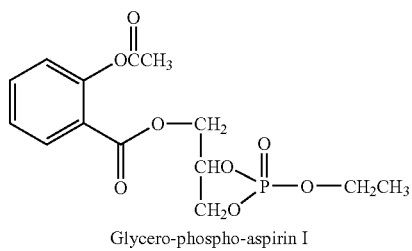

Glycero-phospho-aspirin I

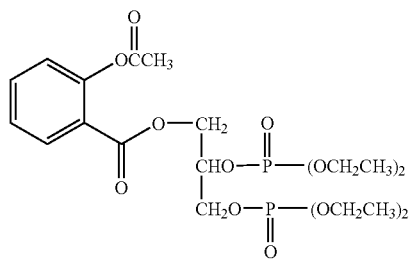

Glycero-phospho-aspirin II

A derivative of naproxen is shown below

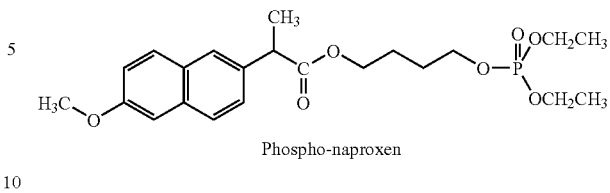

Phospho-naproxen

Example 4

Six Novel NSAID-Based Compounds have Significantly Enhanced Antineoplastic Potency Compared to their Parent Compounds Six compounds based on four representative NSAIDs, aspirin (2 derivatives differing in their linker), ibuprofen, flurbiprofen and sulindac (2 derivatives, differing in the structure of the sulindac moiety) were synthesized following the methodology of Penning et al (Penning T D, Talley J J, Bertenshaw S R, Carter J S, Collins P W, Docter S, et al. Synthesis and biological evaluation of the 1,5-diarylpyrazole class of cyclooxygenase-2 inhibitors: identification of 4-[5-(4-methylphenyl)-3-(trifluoromethyl)-1H-pyrazol-1-yl]benzenesulfonamide (SC-58635, celecoxib). J Med Chem 1997; 40:1347-65.) and the methods described herein. Their structures and NMR profiles are shown above.

Conventional NSAIDs were purchased from Sigma (St Louis, Mo.). We examined these six compounds for their antineoplastic properties, determined in cultured human cells derived from colon, breast and pancreatic cancers.

Cell culture: Human breast (MCF-7 and MDA-MB 231), colon (HT-29, and SW-480) and pancreatic (MIA PaCa-2 and BxPC-3) cell lines (American Type Culture Collection, Manassas, Va.) were grown as monolayers in the specific medium suggested by American Type Culture Collection and supplemented with 10% fetal calf serum (Mediatech, Herndon, Va.), penicillin (50 U/ml) and streptomycin (50 μg/ml; Life Technologies, Grand Island, N.Y.). Cells were incubated at 37° C. in 5% $CO_2$. Cells were seeded at $5.5 \times 10^4$ cells/cm$^2$, allowed to attach overnight, and the following morning cells were treated with each of the test compounds. MCF-7 cells are estrogen receptor positive and MDA-MB231 cells are estrogen receptor negative.

Cell viability assay: We used an assay based on the reduction of 3-(4,5-dimethylthiazol-2-yl)-2,5-diphenyltetrazolium bromide dye (MTT), which was determined according to the manufacture's protocol (Promega, Madison, Wis., USA).

Cell proliferation assay: To determine cell proliferation, we measured the incorporation of 5-bromo-2'-deoxyuridine (BrdU) into newly synthesized cellular DNA, following the manufacture's instructions (BD Biosciences, San Jose, Calif.).

Annexin V and propidium iodide (PI) staining: Cells were seeded at a density of $1 \times 10^5$ cells/well and treated for 24 h with various concentrations of each compound or equivalent volumes of DMSO. Briefly, after incubation with the test compounds, cells were trypsinized and stained with Annexin V-FITC (Invitrogen) and PI (0.5 μg/ml). Following incubation at room temperature for 15 min in the dark, annexin V-FITC and PI fluorescence intensities were analyzed by FACScaliber (BD Bioscience). Annexin V (+)/PI (−) cells are in early apoptosis, annexin V (+)/PI (+) cells are in late apoptosis (secondary necrosis), and annexin V (−)/PI (+) cells are necrotic cells.

Determination of cell cycle phase distribution (PI incorporation assay): Cells were seeded in culture plates and treated for 24 h with various concentrations of each compound or equivalent volumes of DMSO. After treatment, cells were trypsinized and fixed in 70% ethanol for 1 h on ice, stained with PI (50 µg/ml) and RNase A (4 U/ml) for 30 min and subjected to flow cytometric analysis for the determination of their distribution in the cell cycle phases.

The effect of the six compounds and their parent NSAIDs on six human cancer cell lines is summarized in Table 1, which shows 24-h $IC_{50}$s (µM) of the NSAID-derivatives in human cancer cell lines. All six compounds showed enhanced potency in inhibiting cell growth compared to their corresponding conventional NSAIDs. The potency enhancement ranged between >6 and >63-fold (we were unable to obtain a precise $IC_{50}$ for conventional aspirin, given its limited solubility).

TABLE 1

24-h $IC_{50}$, µM

| | BREAST | | COLON | | PANCREATIC | |
|---|---|---|---|---|---|---|
| Compound | MCF-7 | MDA-MB231 | HT29 | SW480 | BxPC-3 | MIA-PaCa-2 |
| Sulindac | 1128 | 530 | 1173 | 900 | 489 | 1036 |
| Phospho-sulindac I | 62 | 17 | 65 | 98 | 62 | 88 |
| Ratio sulindac/PS I | 18 | 31 | 18 | 9 | 8 | 12 |
| Phospho-sulindac II | 38 | 18 | 70 | 73 | 32 | 92 |
| Ratio sullindac/PS II | 30 | 30 | 17 | 12 | 15 | 11 |
| Flurobiprofen | 1433 | 823 | 1670 | 1216 | 825 | 1272 |
| Phospho-Flurobiprofen | 65 | 17 | 80 | 104 | 34 | 135 |
| Ratio flurobiprofen/PF | 22 | 48 | 21 | 12 | 24 | 9 |
| Ibuprofen | 1229 | 748 | 1554 | 1057 | 1064 | 1280 |
| Phospho-Ibuprofen | 79 | 28 | 82 | 75 | 53 | 104 |
| Ratio ibuprofen/PI | 16 | 27 | 19 | 14 | 20 | 12 |
| Aspirin | >2000 | >2000 | 3996 | >2000 | >2000 | >2000 |
| Glyero-phospho-aspirin I | 32 | 199 | 54 | 169 | 63 | 303 |
| Ratio aspirin/GPA I | >63 | >10 | 74 | >12 | >32 | >7 |
| Glycero-phospho-aspirin II | 248 | 360 | 40 | 170 | 38 | 242 |
| Ratio aspirin/GPA II | >8 | >6 | 100 | >12 | >12 | >8 |

Note:
GPA is an abbreviation for glyero-phospho-aspirin

To understand the mechanism by which these compounds inhibited cell growth, we evaluated in MDA-MB 231 human breast cancer cells their effects on cell kinetics, namely cell proliferation (i.e., cell renewal), cell death and cell cycle.

As summarized in Table 2 below, in MDA-MB231 cells, all six compounds, each used at its $IC_{50}$ concentration, a) inhibited cell proliferation between 6% and 50% compared to controls; b) induced both early and late apoptosis, as well as necrosis; and c) inhibited the $G_1$ to S cell cycle phase transition. In this Table, the values for proliferation are the percentage of the corresponding control values. Those for apoptosis and necrosis refer to the percentage of cells in each category with respect to the entire cell population, and are to be compared to the control (vehicle only-treated) cells (uppermost row).

TABLE 2

Cell kinetic effect of six compounds

| Compound | Proliferation (% control) | Early apoptosis (%) | Late apoptosis (%) | Necrosis (%) |
|---|---|---|---|---|
| Control | N/A | 1.4 | 2.0 | 0.6 |
| Phospho-sulindac I | 52 | 1.7 | 4.7 | 1.1 |

TABLE 2-continued

Cell kinetic effect of six compounds

| Compound | Proliferation (% control) | Early apoptosis (%) | Late apoptosis (%) | Necrosis (%) |
|---|---|---|---|---|
| Phospho-sulindac II | 52 | 5.0 | 23.2 | 2.6 |
| Phospho-flurbiprofen | 42 | 5.3 | 20.6 | 1.7 |
| Phospho-ibuprofen | 50 | 7.4 | 43.2 | 5.6 |
| Glycero-phospho-aspirin I | 94 | 4.8 | 3.2 | 0.3 |

TABLE 2-continued

Cell kinetic effect of six compounds

| Compound | Proliferation (% control) | Early apoptosis (%) | Late apoptosis (%) | Necrosis (%) |
|---|---|---|---|---|
| Glycero-phospho-aspirin II | 52 | 2.4 | 2.2 | 0.4 |

Following identical methodologies as those described above for MDA-MB231 cells, we determined the effect of phospho-sulindac I on the cell kinetics of SW480 and HT-29 human colon cancer cells by treating them for 24 h with phospho-sulindac I used at its 24-h $IC_{50}$ concentration. Compared to untreated controls, phospho-sulindac I at a concentration equal to its IC50 for growth at 24 h: inhibited cell proliferation by 72% (from 43% in controls to 12% in phospho-sulindac I treated cells); induced apoptosis (early and late subtypes combined) by 201% (from 6.6% to 20%); induced necrosis by 1350% (from 0.2% to 2.9%) and blocked the transition form the G1 to the S cell cycle phase

Example 5

Phospho-Sulindac I Inhibits Colon Cancer Growth in vivo

The effect of phospho-sulindac I on tumor growth in vivo was evaluated in two animal models of colon cancer, $APC^{Min/+}$ mice and colon cancer xenografts in nude mice.

$APC^{Min/+}$ mice study: Min mice have a truncating mutation in the Apc gene that predisposes them to the development of gastrointestinal tumors in the small intestine and colon (Lipkin M, Yang K, Edelmann W, et al. Preclinical mouse models for cancer chemoprevention studies. Ann NY Acad Sci 1999; 889:14-9.). In many important ways, this model system represents a useful (and extensively utilized) experimental system that recapitulates the relevant steps of colon carcinogenesis.

Eleven week-old male C57BL/6J $APC^{Min/+}$ mice divided into four groups of 10 mice/group were treated for 4 weeks via gavage administration as follows: group 1 was treated with vehicle (corn oil); and group 2 was treated with phospho-sulindac I 50 mg/kg/day. At the end of treatment, compared with vehicle-treated controls, phospho-sulindac I decreased the number of tumors in the small intestine by 57.2% ($p<0.002$) (number of intestinal tumors in vehicle-treated group 33.6±8.7, and in phospho-sulindac I treated mice 19.4±12.0), whereas, specifically, in the colon the reduction by phospho-sulindac I was of 61.8% ($p<0.02$) compared to vehicle treated mice (number of colon tumors in vehicle-treated group 1.6±0.8, and in phospho-sulindac I treated mice 0.6±0.5). Of note, as we have shown, conventional sulindac stimulates the formation of tumors in the colon of Min mice (Yang K, Fan K, Kurihara N, et al. Regional response leading to tumorigenesis after sulindac in small and large intestine of mice with Apc mutations. Carcinogenesis 2003; 24(3):605-11). Our results document that P-S exerts a profound inhibitory effect on intestinal carcinogenesis in Min mice without any overt signs of toxicity.

Nude mice xenograft study: Female nude mice CByJ.Cg-Foxn1 (5-6 weeks-old) were inoculated subcutaneously in their lower right flank with $1.5 \times 10^6$ SW480 colon cancer cells in a volume of 100 µl (containing 50% matrigel in PBS). Seven days later, animals were randomized into two groups (8 mice/group): group 1 received vehicle (1% (w/v) carboxy methylcellulose); group 2 received 50 mg/kg/day phospho-sulindac I. All drugs were administered in a solution of 1% (w/v) carboxy methylcellulose by gavage once daily (phospho-sulindac I and sulindac concentrations are equimolar). Tumors were measured twice a week with a digital microcaliper, and tumor volume (TV) was calculated using the formula: $TV=[L \times W \times (L+W/2) \times 0.56]$, where L=length and W=width of tumor. After 14 days of treatment, animals were sacrificed, and tumors were removed and weighed. The mean tumor weight for vehicle and phospho-sulindac I were 0.246±0.041 and 0.097±0.018 (mean±SEM), respectively, indicating a reduction in tumor weigh of 60% ($p<0.05$) by phospho-sulindac I. Of note, phospho-sulindac I was well tolerated, since no weight loss or other signs of toxicity were observed throughout the treatment period.

Synergy Between Difluoromethylornithine (DFMO) and Phospho-Sulindac

We examined the potential synergy between (DFMO) and phospho-sulindac I. A significant development in combination chemoprevention is the use of sulindac plus DFMO to prevent colon cancer (Gerner et al. A comprehensive strategy to combat colon cancer targeting the adenomatous polyposis coli tumor suppressor gene. Ann N Y Acad Sci 2005; 1059: 97-105; Gerner E W, Meyskens F L, Jr. Polyamines and cancer: old molecules, new understanding. Nat Rev Cancer 2004; 4(10):781-92; Gerner E W, Meyskens F L, Jr., Goldschmid S, Lance P, Pelot D. Rationale for, and design of, a clinical trial targeting polyamine metabolism for colon cancer chemoprevention. Amino Acids 2007; 33(2):189-95.). The rationale for this combination is simple yet quite powerful: DFMO inhibits the enzyme ornithine decarboxylase, which catalyzes the rate-limiting step in polyamine synthesis, while sulindac stimulates polyamine acetylation and export from the cell by acting on the enzyme spermidine/spermine $N^1$-acetyltransferase (SSAT). The end result is reduced polyamine levels leading to suppressed growth of cancer cells. A recently published large clinical trial demonstrated that DFMO plus sulindac reduced the recurrence of all adenomas by 69% and of advanced adenomas by 92% (Meyskens F L, McLaren C E, Pelot D, et al. Difluoromethylornithine Plus Sulindac for the Prevention of Sporadic Colorectal Adenomas: A Randomized Placebo-Controlled, Double-Blind Trial. Cancer Prevention Research Published Online First on Apr. 14, 2008 as 10.1158/1940-6207.CAPR-08-0042.).

Figure 2A:
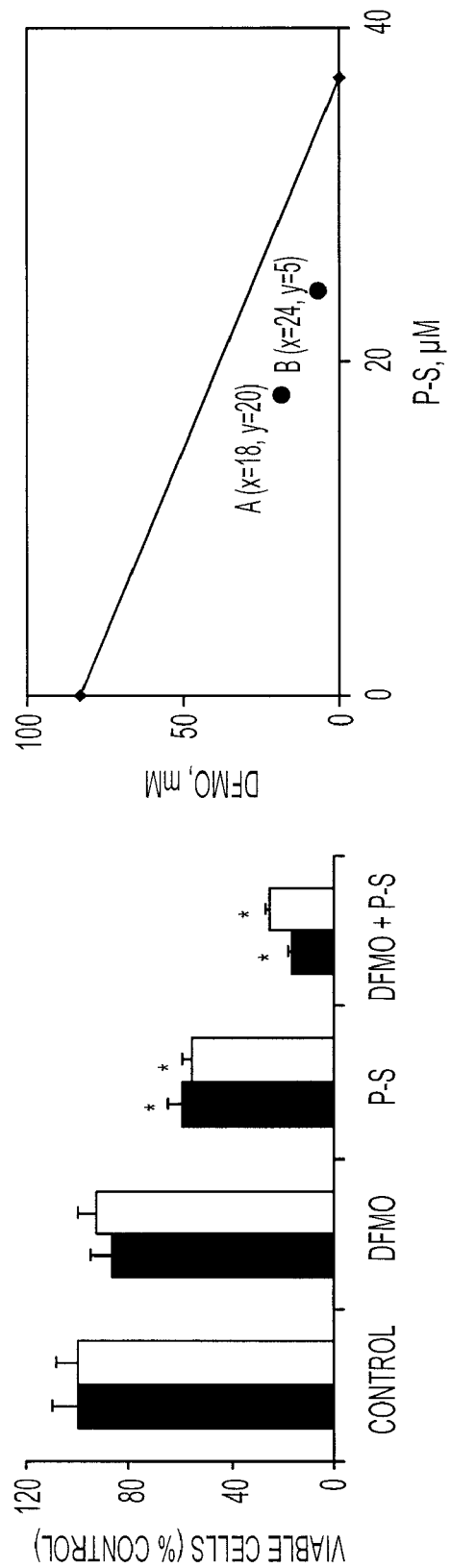

To evaluate the potential synergy between phospho-sulindac I and DFMO we used HT-29 and SW480 human colon cancer cells and employed the methodologies described above. As shown in FIG. 2A, in both HT-29 and SW480 cells DFMO 5 mM and phospho-sulindac I 40 µM each alone inhibited modestly cell growth at 48 h, but their combination was more effective than the sum of the two: a) in HT-29 cells the reductions in cell number were: DFMO 14%, P-S 41%, both 84%; and b) in SW480 cells: DFMO 8%, P-S 45%, both 75%. Examined by isobologram (Tallarida R J, Porreca F, Cowan A. Statistical analysis of drug-drug and site-site interactions with isobolograms. Life Sci 1989; 45(11):947-61), the combined effects of DFMO and P-S on cell growth represent pharmacological synergy.

Figure 2B:
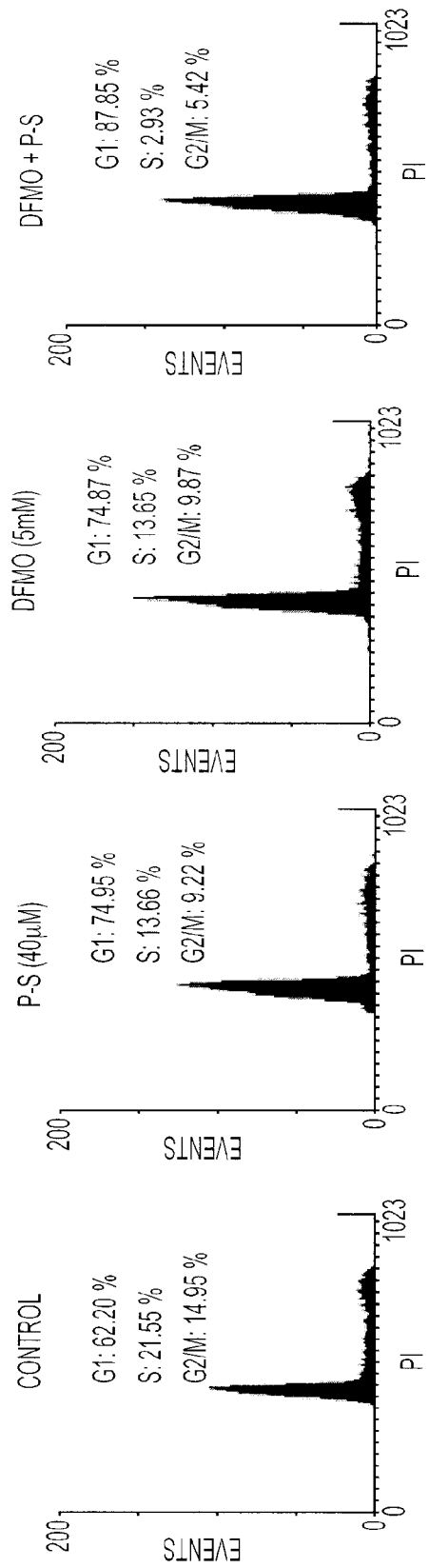
Figure 2C:
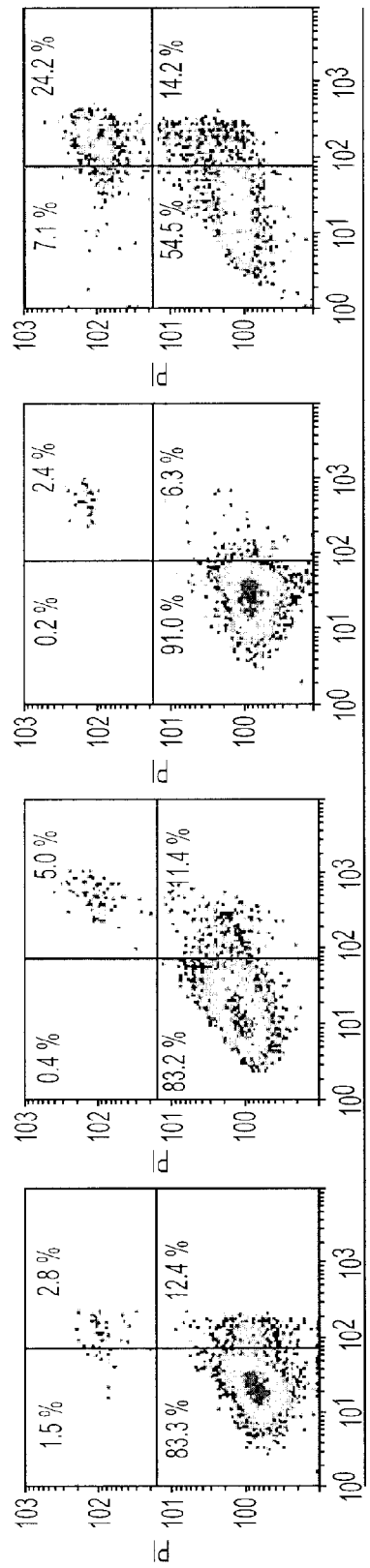
Figure 3:
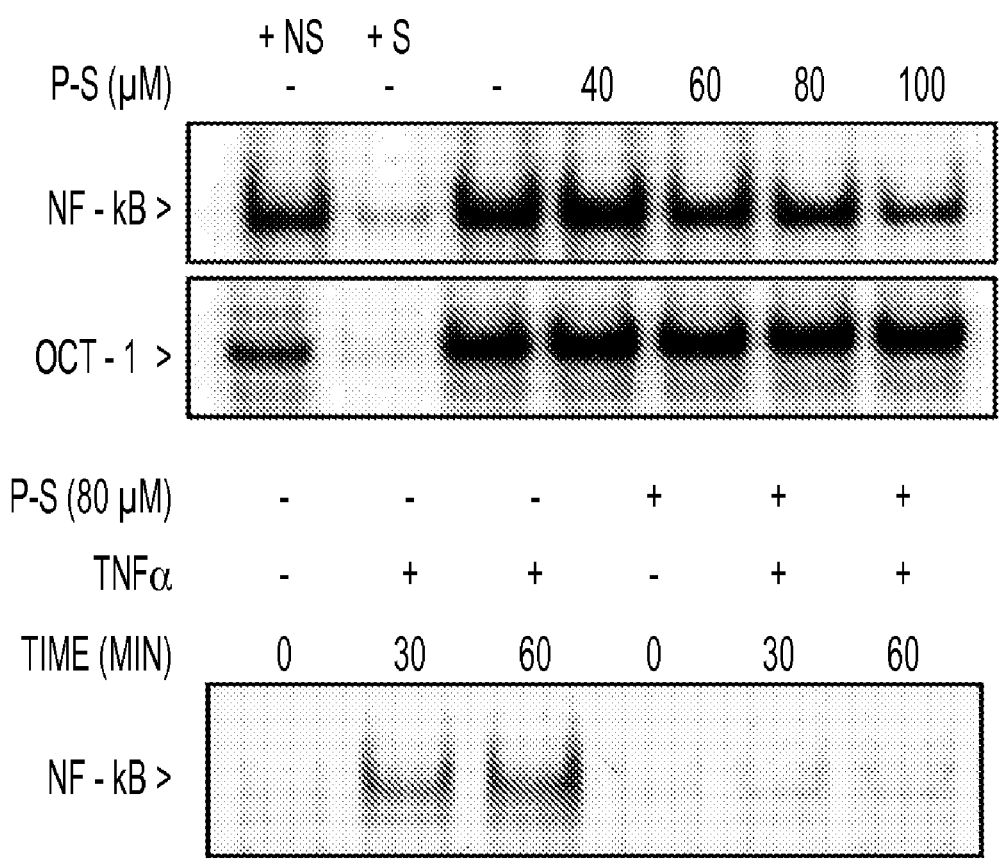
Figure 4:
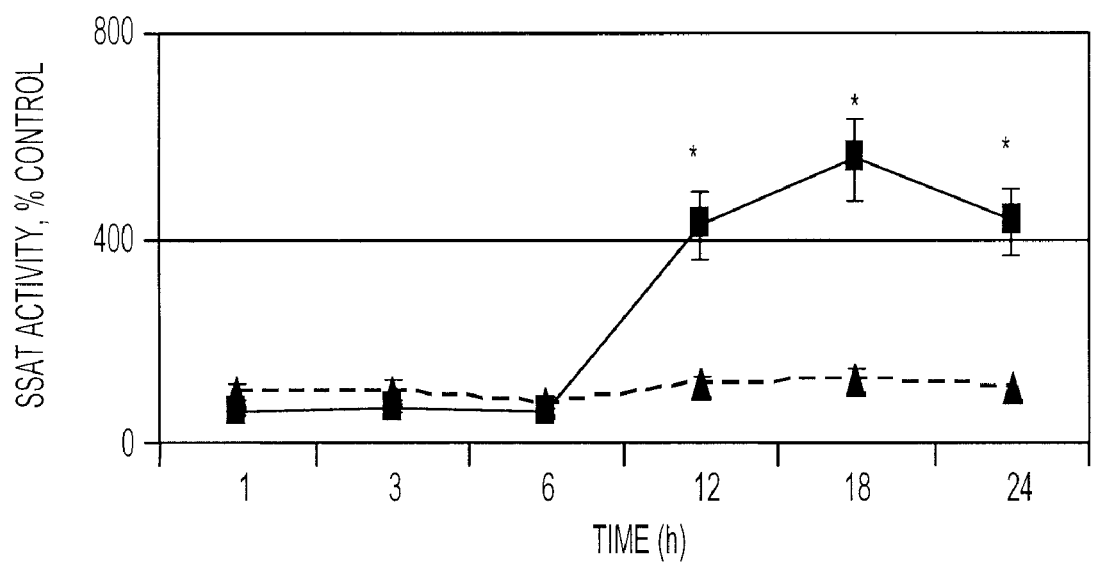

We then examined the effect of the synergy between the two compounds on cell kinetic parameters. Cell cycle analysis showed that the combination of DFMO and phospho-sulindac I enhances the magnitude of the effect (S phase: 13.6% for either alone is reduced to 2.9% for both). In addition, the combination of DFMO and phospho-sulindac I presented a G1 population arrest of 88% compared to the 75% of either DFMO or phospho-sulindac I alone (FIG. 2B). Furthermore, we examined whether DFMO increased phospho-sulindac I-induced apoptosis in colon cancer cells. After 48 h of incubation with DFMO and phospho-sulindac I, the percentage of apoptotic cells was 38.4%, compared to 8.7% and 16.5% for DFMO and phospho-sulindac I alone, respectively (FIG. 2C). Of note, the concentrations of both compounds were below their $IC_{50}$s for cell growth.

Further evidence of the synergy between the two compounds was provided by their effect on polyamine levels. Conventional sulindac is known to reduce polyamine levels in colon cancer cells (Yerushalmi et al. Role of polyamines in arginine-dependent colon carcinogenesis in Apc(Min) (/+) mice. Mol Carcinog 2006; 45(10):764-73.; Choi et al. Combination of 5-fluorouracil and N1,N11-diethylnorspermine markedly activates spermidine/spermine N1-acetyltransferase expression, depletes polyamines, and synergistically induces apoptosis in colon carcinoma cells. J Biol Chem 2005; 280(5):3295-304; and Basuroy and Gerner. Emerging concepts in targeting the polyamine metabolic pathway in epithelial cancer chemoprevention and chemotherapy. J Biochem (Tokyo) 2006; 139(1):27-33). Phospho-sulindac I markedly diminished the levels of spermidine (34% of control values) and spermine (9% of control values) in SW480 cells, without significantly affecting those of putrescine (91% of control values), the first polyamine in their biosynthetic pathway (ornithine→putrescine→spermidine→spermine).

Figures 1, 1A, 2, 3:
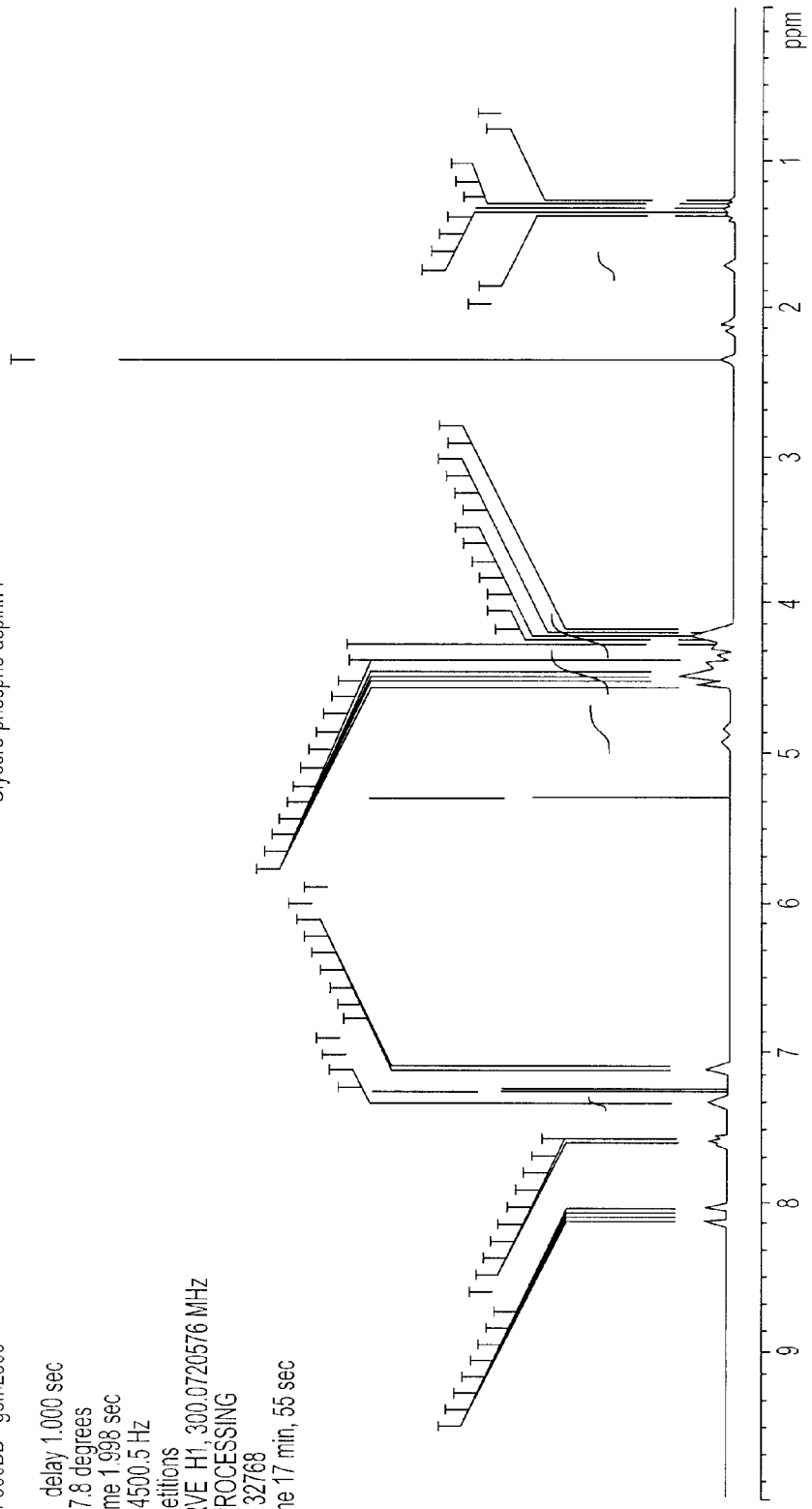
FIG. 3 shows that phospho-sulindac I inhibits NF-κB activation in colon cancer cells. Phospho-sulindac inhibits constitutive and TNFα-induced NF-κB activation. Upper panel: Nuclear fractions were isolated from HT-29 cells after 4 h of incubation in the absence or in the presence of 40-100 µM phospho-sulindac I (P-S). Electrophoretic mobility shift assay (EMSA) for NF-κB and OCT-1 from cells treated with various concentrations of phospho-sulindac I. To determine the specificity of each transcription factor-DNA complex, the control nuclear fraction (−) was incubated in the presence of 100-fold molar excess of unlabeled oligonucleotide containing the consensus sequence for either the specific (+S) or a nonspecific (+NS) transcription factor before the binding assay. Lower panel: Nuclear fractions were isolated from HT-29 cells, after 4 h of preincubation in the absence or in the presence of 80 µM phospho-sulindac I (P-S) and further 0, 30 or 60 min incubation without (−) or with 10 ng/ml TNFα. EMSA for NF-κB incubated with various concentrations of phospho-sulindac I.
Figures 1, 1A, 2, 3, 4:
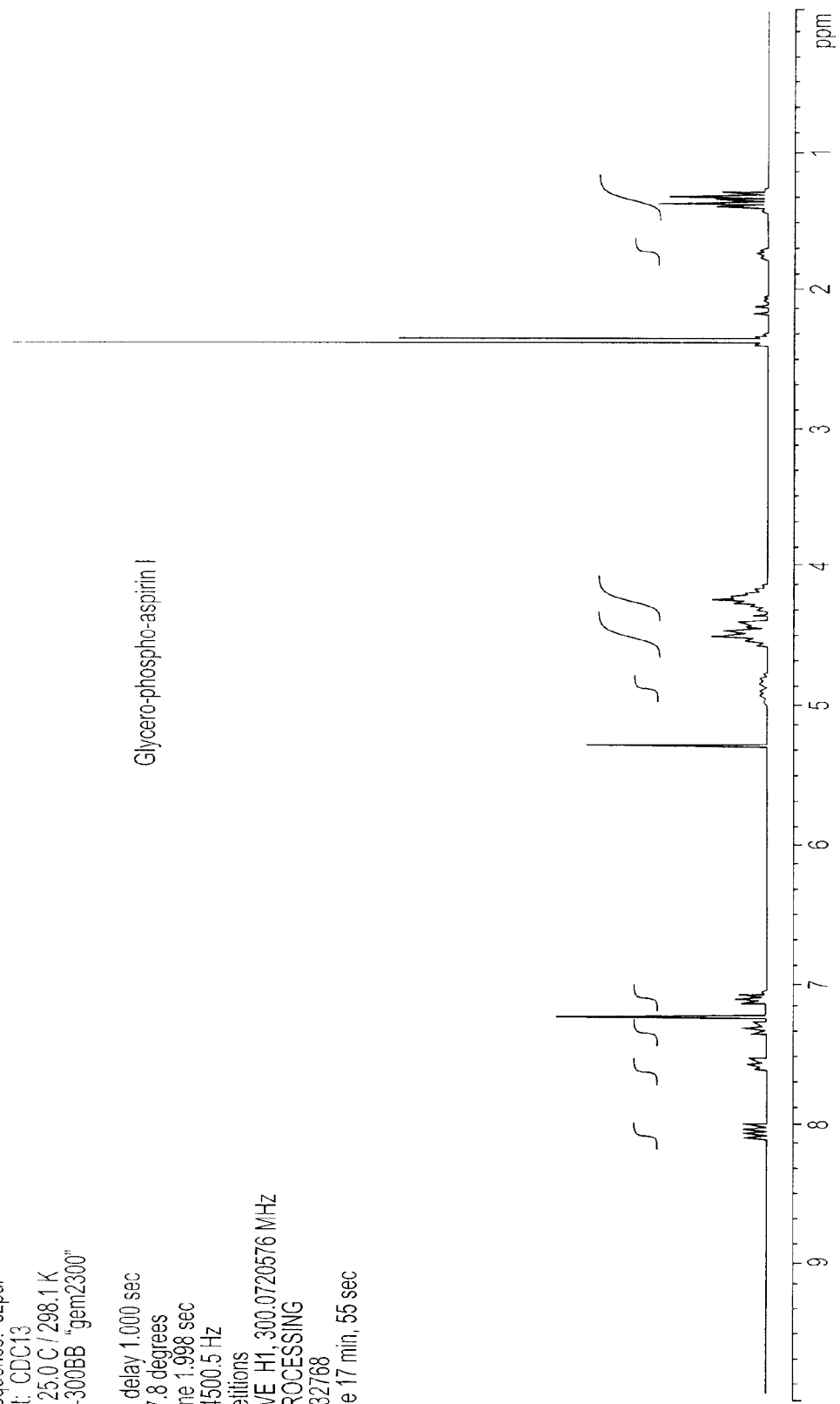
FIG. 4 shows that Phospho-sulindac I induces SSAT enzymatic activity in colon cancer cells. SW480 cells were incubated without or with phospho-sulindac I (P-S) for up to 24 h and SSAT activity was determined at each time point by determining the amount of labelled N1-acetylspermidine synthesized from [$^{14}$C]acetyl-CoA and unlabeled spermidine. Values are shown as means±SEM of 4 independent experiments. *Significantly different from control cells ($p<0.01$, one way ANOVA test).
Figures 1, 1A, 2, 3, 4, 5:
Figures 1, 1A, 2, 3, 4, 5, 6:
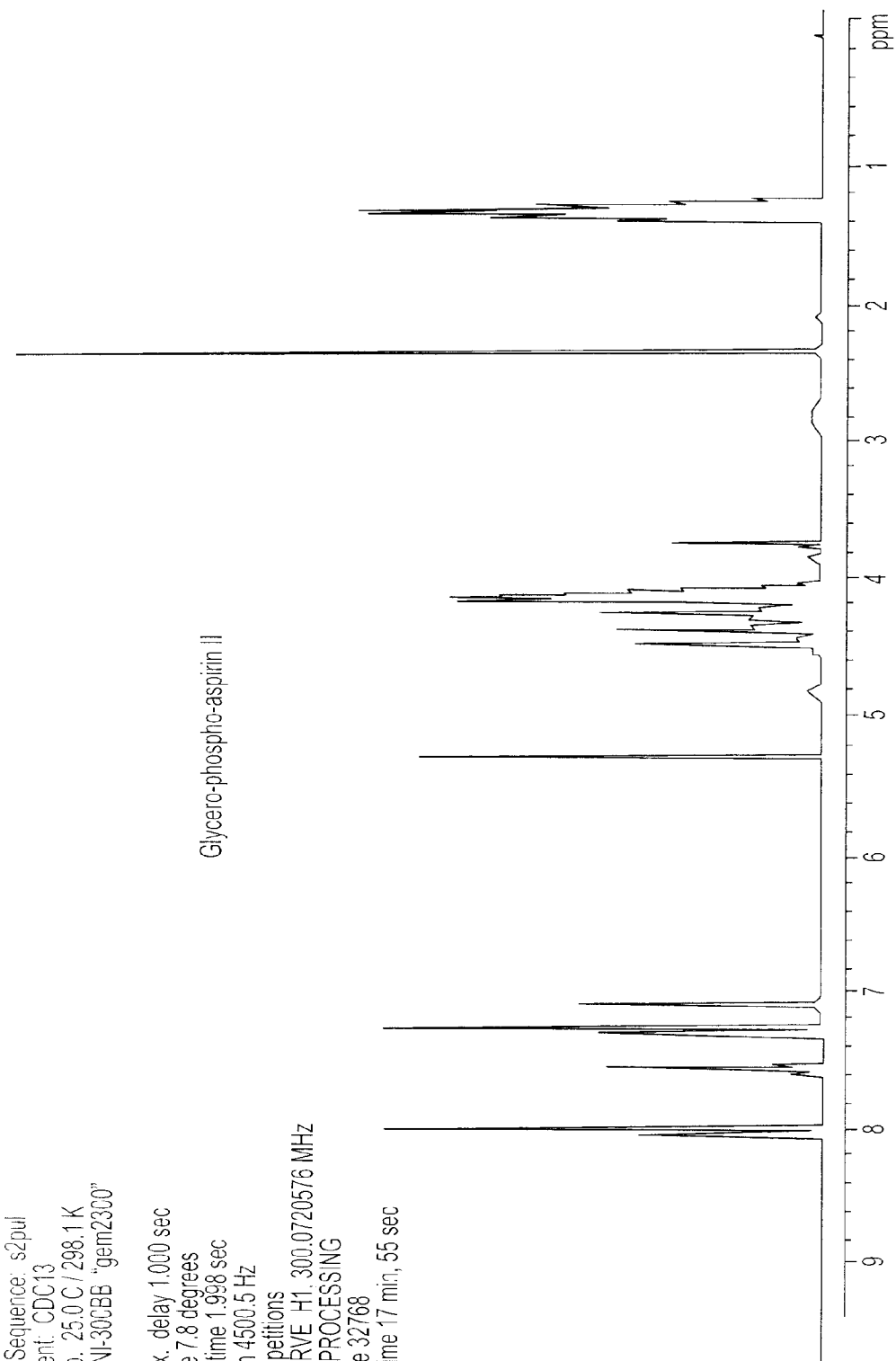
Figures 1, 1B, 2:
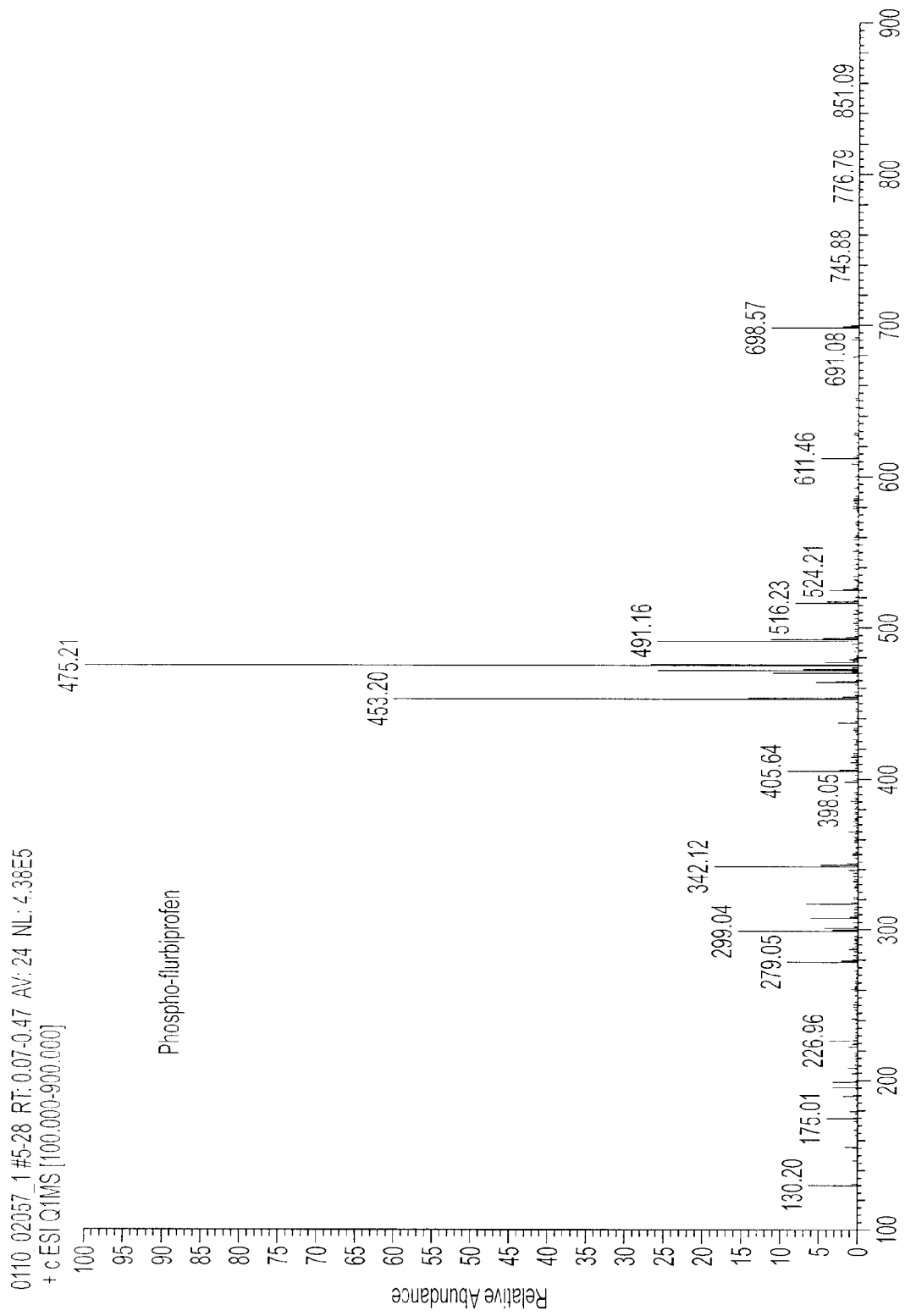
Figures 1, 1B, 2, 3:
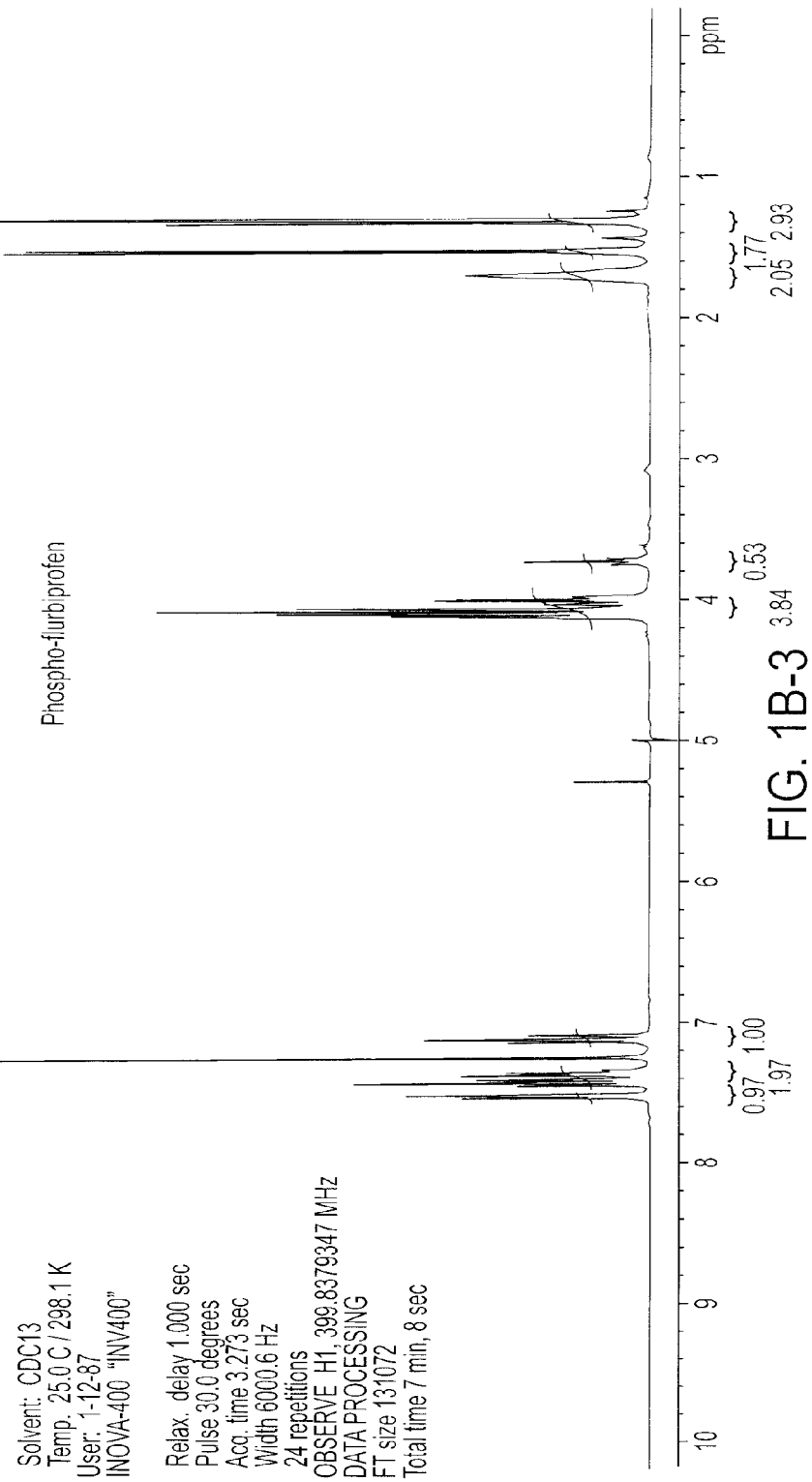

The effect of phospho-sulindac I on polyamines is mediated, at least in part, by activation of SSAT by phospho-sulindac I. It is known that conventional sulindac induces SSAT activity (Babbar et al., Cyclooxygenase-independent induction of apoptosis by sulindac sulfone is mediated by polyamines in colon cancer. J Biol Chem 2003; 278(48): 47762-75.). Incubation of HT-29 and SW480 cells with 85 μM phospho-sulindac I for 24 h leads to a 3- and 4.4-fold increase of SSAT activity (P<0.05 versus control), respectively. On the other hand, incubation with sulindac led to a 1.5 and 2.5-fold increase of SSAT activity (P<0.05 versus control) in HT-29 and SW480 cells, respectively. Examination of the time dependence of the induction of SSAT in SW480 cells exposed to 85 μM phospho-sulindac I revealed after 12 h of incubation, a 4-fold induction of SSAT compared to vehicle-treated controls, which continued to a maximum of 5.5-fold increase after 18 h of incubation (see FIG. 4).

The Anti-Inflammatory Effect of Phospho-Sulindac I; Inhibition of NF-κb Activation The anti-inflammatory effect of phospho-sulindac I was examined by evaluating its effect on the activation of nuclear factor-kappa B (NF-κB), a protein complex that is a transcription factor. NF-κB is found in almost all animal cell types and is involved in cellular responses to stimuli such as stress, cytokines, free radicals, ultraviolet irradiation, oxidized LDL, and bacterial or viral antigens (Gilmore TD (1999). "The Rel/NF-kappaB signal transduction pathway: introduction". Oncogene 18 (49): 6842-4). NF-κB plays a key role in regulating the immune response to infection. Consistent with this role, incorrect regulation of NF-κB has been linked to cancer, inflammatory and autoimmune diseases, septic shock, viral infection, and improper immune development. NF-κB has also been implicated in processes of synaptic plasticity and memory (Albensi B C, Mattson M P (2000). "Evidence for the involvement of TNF and NF-kappaB in hippocampal synaptic plasticity". *Synapse* 35 (2): 151-9). In general, NF-κB represents a major molecular control of inflammation. Of additional interest is the modulating effect of NF-κB on cell growth and inflammation, especially in the context of cancer (Zhang Z, Rigas B. NF-kappaB, inflammation and pancreatic carcinogenesis: NF-kappaB as a chemoprevention target (review). Int J Oncol 2006; 29(1):185-92; Karin M, Greten FR. NF-kappaB: linking inflammation and immunity to cancer development and progression. Nat Rev Immunol 2005; 5(10):749-59).

We investigated whether phospho-sulindac I affects the activation of NF-κB in HT-29 human colon cancer cells, using electrophoretic mobility shift assays. As also demonstrated in FIG. 3, we found that treatment of HT-29 cells with phospho-sulindac I suppressed the constitutively active NF-κB in a concentration-dependent manner. Furthermore, NF-κB activation was rapidly induced by exposure to tumor necrosis factor alpha (TNFα) in HT-29 cells; however, 4 h pre-incubation with 80 μM phospho-sulindac I abrogated this effect).

The Safety of Phospho-Sulindac I

We assessed the safety of phospho-sulindac I by examining its genotoxicity by the Ames test and its gastrointestinal and other toxicity by performing a toxicological study in mice.

Phospho-sulindac I lacked genotoxicity, as demonstrated by a mutagenicity assay performed by the BioReliance Laboratory (Rockville Md.) that conducts such assays under high-quality standardized Good Laboratory Practices conditions. The mutagenic potential of phospho-sulindac I was evaluated by measuring its ability to induce reverse mutations at selected loci of two strains of *Salmonella typhimurium* in the presence and absence of S9 activation. All these studies were negative for genotoxicity.

Phospho-sulindac I lacked gastrointestinal toxicity in mice; gastrointestinal toxicity is the major side effect of sulindac as well as of the entire class of NSAIDs. We evaluated in mice the potential toxicity of phospho-sulindac I. Three groups, each consisting of 8 female C57BL/6J+/+mice 6 wks of age, were treated for 5 days by oral gavage with equimolar amounts of phospho-sulindac I (317 mg/kg/d) or conventional sulindac (200 mg/kg/day) or vehicle. Mice were weighed at time 0 and on days 3 and 5. Mice surviving to the end of the study were euthanized and necropsied.

Phospho-sulindac I- and vehicle-treated mice a) maintained their weight (phospho-sulindac I=16.3±1.2→15.7±1.2; vehicle=16.1±1.0 g→15.7±1.2, mean±SD); b) showed no evidence of gastrointestinal or other toxicity; c) all were alive at the conclusion of the study and appeared healthy; and d) inspection of the heart, lungs, spleen, kidneys and liver showed no abnormalities. In contrast, sulindac-treated mice a) lost 20% of their weight (16.3±1.2 g→13.0±0.5 g; mean±SD); b) showed significant mortality: 75% vs. 0% for phospho-sulindac I and vehicle (5 of the 8 mice died:1 on day 2; 2 on day 3; 2 on day 4; and 1 on day 5), and c) necropsies revealed upper gastrointestinal toxicity with macroscopically evident gastric ulcers in 3, gastric bleeding in 1, and perforation in 1. The stomachs of sulindac-treated animals were larger than those of the other two groups and in some the liver appeared hyperemic.

Example 6

Phosphovalproic Acid Inhibits the Growth of Various Human Cancer Cell Lines More Potently than Conventional Valproic Acid Valproic acid (VPA) is a in clinical use primarily as an anticonvulsant and mood-stabilizing drug, is now being extensively studied as a potent anticancer agent, especially since it was found to inhibit histone deacetylation (Abend N S, Dlugos D J. Treatment of refractory status epilepticus: literature review and a proposed protocol. Pediatr Neurol. 2008 June; 38(6):377-90; Oki Y. Issa J P. Review: recent clinical trials in epigenetic therapy. Rev Recent Clin Trials. 2006 May; 1 (2):169-82; Barzman D H, Findling R L. Pharmacological treatment of pathologic aggression in children. Int Rev Psychiatry. 2008 April; 20(2):151-7). VPA has shown potent antitumor effects in several in vitro and in vivo systems, and encouraging results have been reported from early clinical trials (Duenas-Gonzalez A, Candelaria M, Perez-Plascencia C, Perez-Cardenas E, de la Cruz-Hernandez E, Herrera LA. Valproic acid as epigenetic cancer drug: preclinical, clinical and transcriptional effects on solid tumors. *Cancer Treat Rev.* 2008 May; 34(3):206-22.).

We synthesized phosphovalproic acid (phosph-VPA), a derivative of VPA, following the methodology described for phospho-sulindac I above and determined its effect on cell growth by determining its 24-h $IC_{50}$ also according to the methods described above. Conventional valproic acid was also studied for comparison purposes. The structure of phosphovalproic acid is:

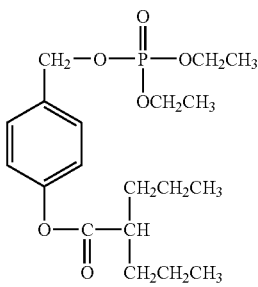

The results summarized in Table 3, demonstrate that phosphovalproic acid a) is very potent in inhibiting the growth of several human cancer cell lines, and b) shows enhanced potency in inhibiting cell growth compared to conventional VPA, with the potency enhancement ranging between 35 and 245-fold.

TABLE 3

Phospho-valproic acid inhibits the growth of human cancer cells ($IC_{50}$, µM)

| Cell line | VPA | Phosoho-VPA | Fold Enhancement |
|---|---|---|---|
| Breast | | | |
| MCF-7 | 1,775 | 51 | 35 |
| MDA-MB231 | 4,049 | 30 | 136 |
| Colon | | | |
| HT-29 | 3,210 | 13 | 245 |
| SW480 | 3,639 | 59 | 62 |
| Pancreas | | | |
| BxPC-3 | 1,680 | 36 | 47 |
| MIA PaCa2 | 3,082 | 89 | 35 |

These values are representative of two experiments, each performed in quintuplicate; results were within 10%.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof. Furthermore, the teachings and disclosures of all references cited herein are expressly incorporated in their entireties by reference.

What is claimed is:

1. A compound selected from the group consisting of

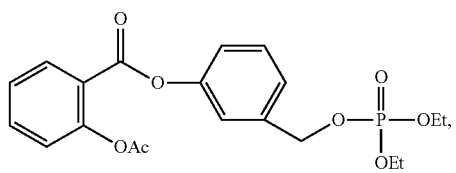

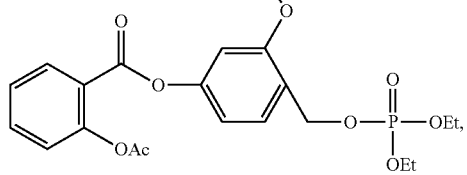

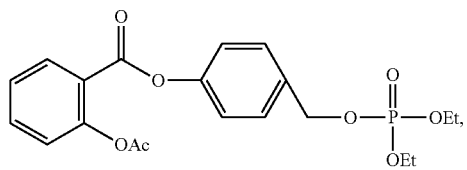

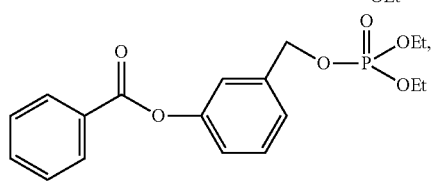

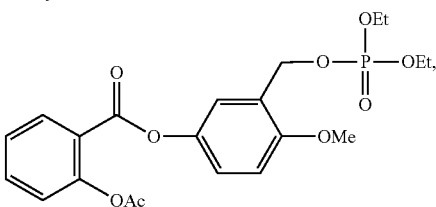

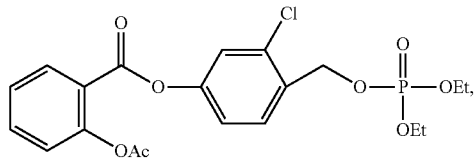

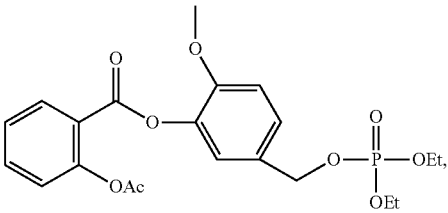

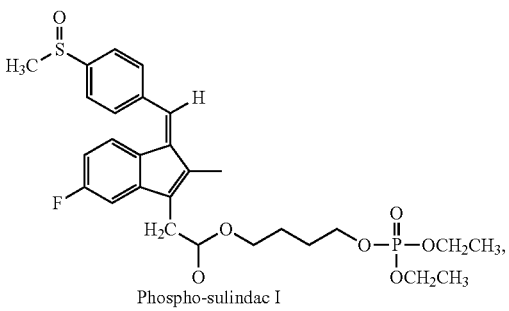

Phospho-sulindac I

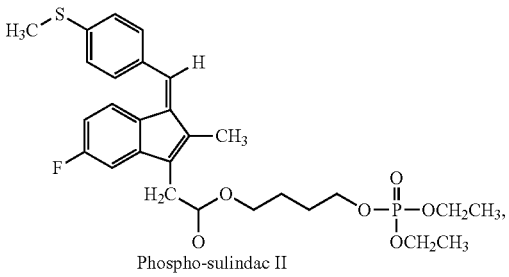

Phospho-sulindac II

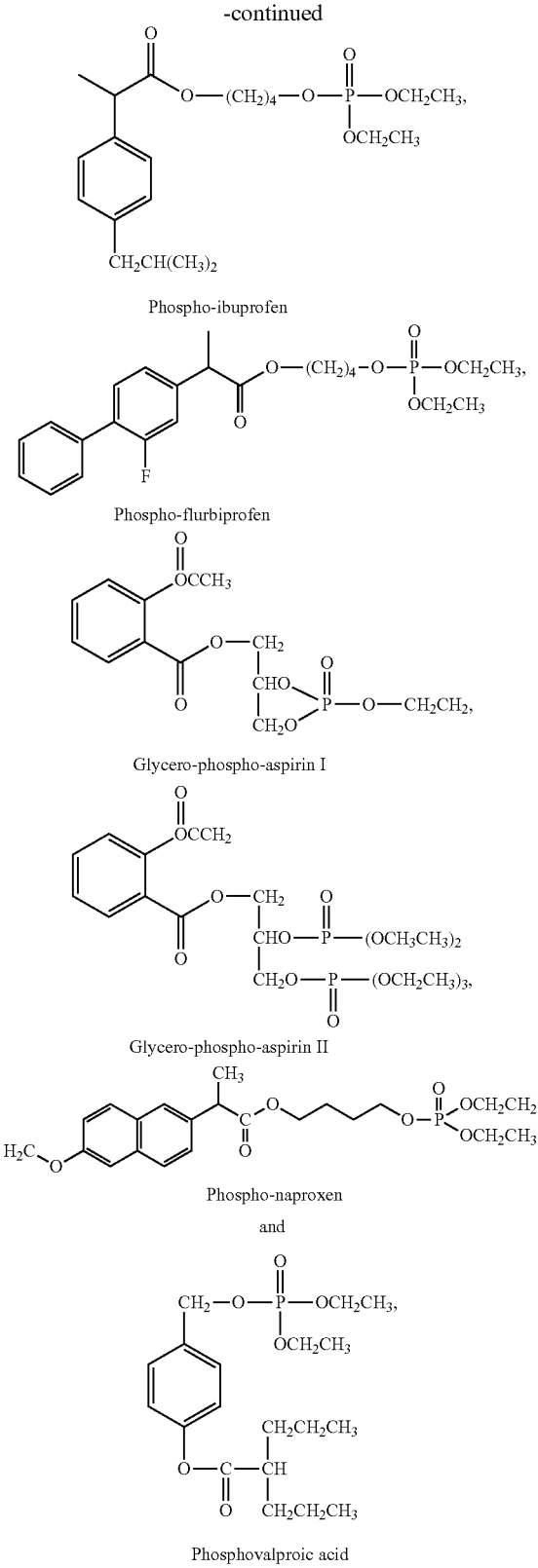

or a pharmaceutically acceptable salt of said compound.

2. A pharmaceutical composition comprising a compound or pharmaceutically acceptable salt thereof according to claim 1 and a pharmaceutically acceptable excipient.

3. The compound or pharmaceutically acceptable salt thereof of claim 1, wherein the compound is selected from the group consisting of Phospho-sulindac I and Phospho-sulindac II.

4. The compound or pharmaceutically acceptable salt thereof of claim 1, wherein the compound is Phospho-sulindac I.

5. The compound or pharmaceutically acceptable salt thereof of claim 1, wherein the compound is Phospho-sulindac II.

6. The compound or pharmaceutically acceptable salt thereof of claim 1, wherein the compound is Phospho-ibuprofen.

7. The compound or pharmaceutically acceptable salt thereof of claim 1, wherein the compound is Phospho-aspirin I.

8. The compound or pharmaceutically acceptable salt thereof of claim 1, wherein the compound is Glycero-phospho-aspirin II.

9. The compound or pharmaceutically acceptable salt thereof of claim 1, wherein the compound is

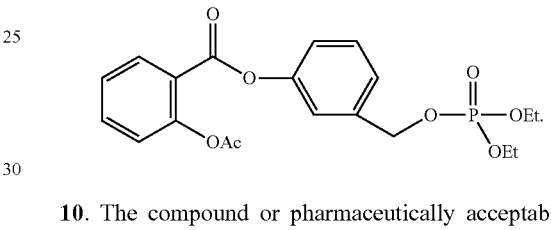

10. The compound or pharmaceutically acceptable salt thereof of claim 1, wherein the compound is

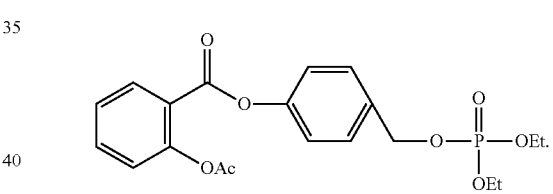

11. The compound or pharmaceutically acceptable salt thereof of claim 1, wherein the compound is

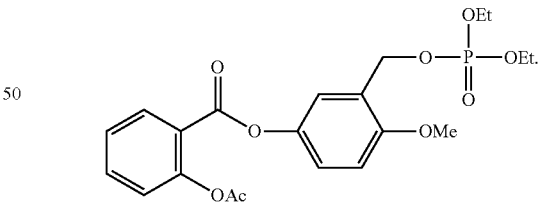

12. The compound or pharmaceutically acceptable salt thereof of claim 1, wherein the compound is

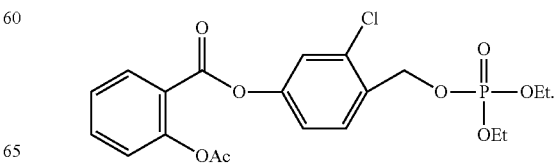

13. The pharmaceutical composition of claim 2, wherein said compound or pharmaceutically acceptable salt thereof is Phospho-sulindac I.

14. The pharmaceutical composition of claim 2, wherein said compound or pharmaceutically acceptable salt thereof is Phospho-sulindac II.

15. The pharmaceutical composition of claim 2, wherein said compound or pharmaceutically acceptable salt thereof is Phospho-ibuprofen.

16. The pharmaceutical composition of claim 2, wherein said compound or pharmaceutically acceptable salt thereof is Phospho-aspirin I.

17. The pharmaceutical composition of claim 2, wherein said compound or pharmaceutically acceptable salt thereof is Glycero-phospho-aspirin II.

18. The pharmaceutical composition of claim 2, wherein said compound or pharmaceutically acceptable salt thereof is

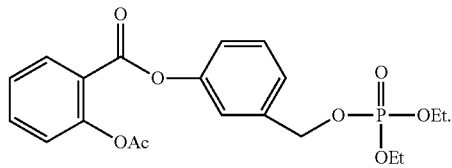

19. The pharmaceutical composition of claim 2, wherein said compound or pharmaceutically acceptable salt thereof is

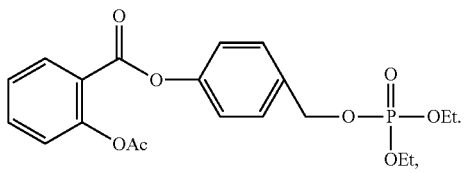

20. The pharmaceutical composition of claim 2, wherein said compound or pharmaceutically acceptable salt thereof is

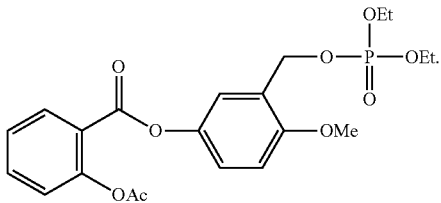

21. The pharmaceutical composition of claim 2, wherein said compound or pharmaceutically acceptable salt thereof is

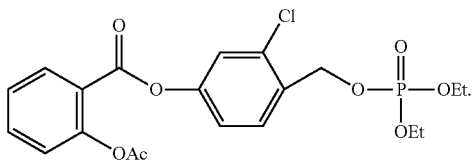

* * * * *

UNITED STATES PATENT AND TRADEMARK OFFICE
CERTIFICATE OF CORRECTION

PATENT NO. : 8,236,820 B2  Page 1 of 4
APPLICATION NO. : 12/189500
DATED : August 7, 2012
INVENTOR(S) : Basil Rigas It is certified that error appears in the above-identified patent and that said Letters Patent is hereby corrected as shown below:

In the Claims

Column 40, line 50, claim 1, the structure:

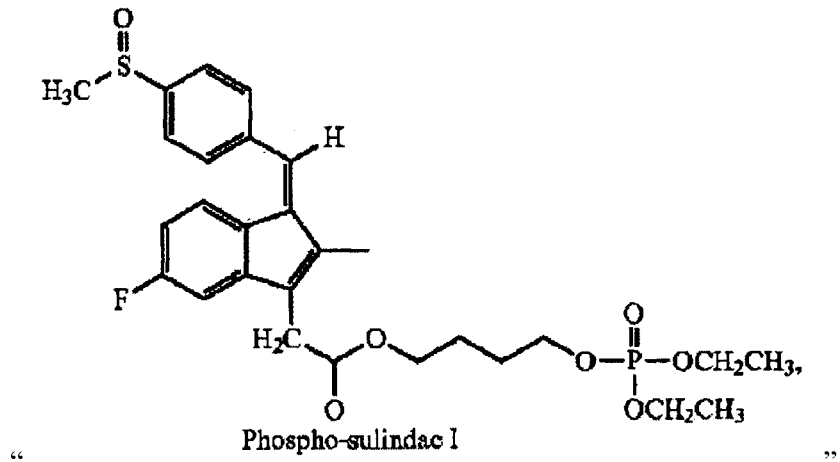

should be replaced by the following structure:

Signed and Sealed this
Twenty-first Day of October, 2014

Michelle K. Lee
*Deputy Director of the United States Patent and Trademark Office*

CERTIFICATE OF CORRECTION (continued)
U.S. Pat. No. 8,236,820 B2

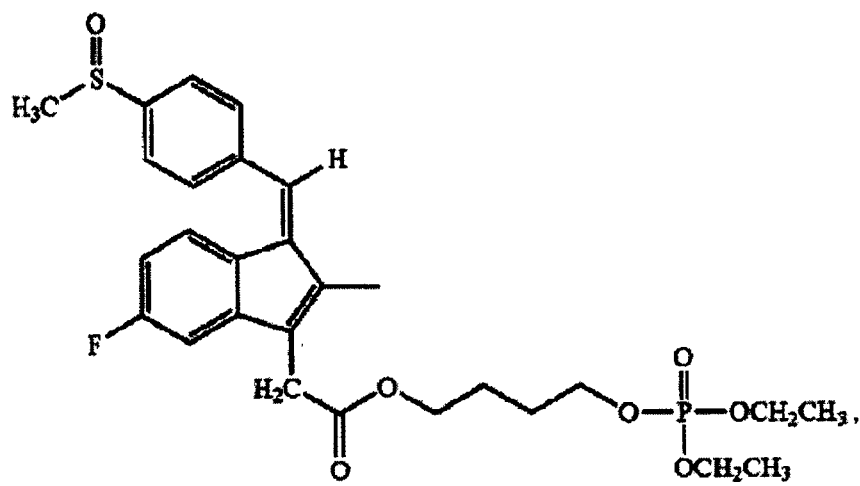

Phospho-sulindac I

Column 40, line 60, claim 1, the structure:

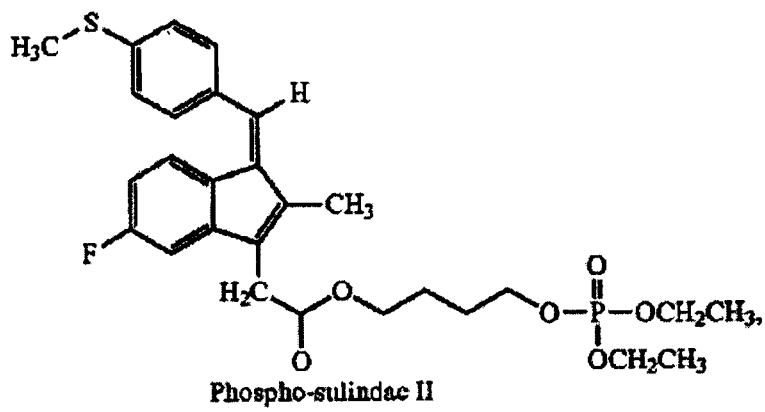

" Phospho-sulindac II "

should be replaced by the following structure:

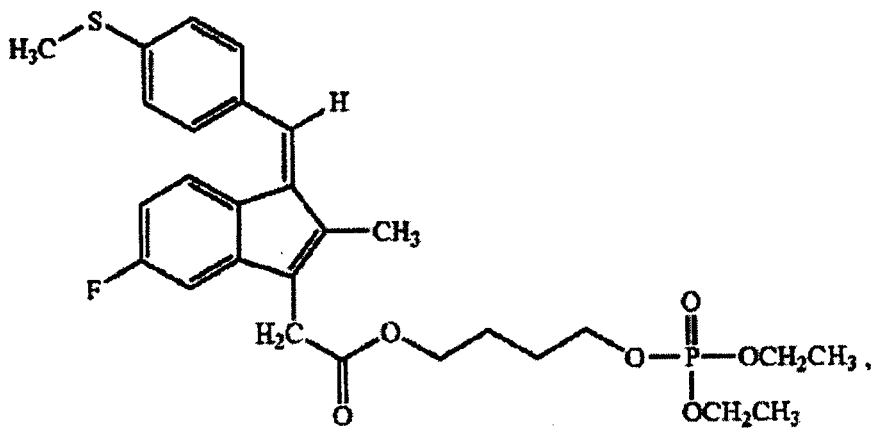

Phospho-sulindac II

Column 41, line 25, claim 1, the structure:
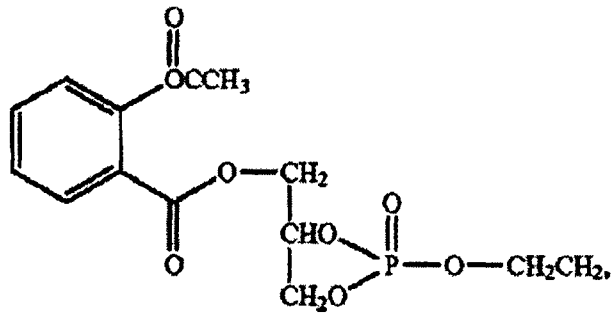
" Glycero-phospho-aspirin I "
should be replaced by the following structure:
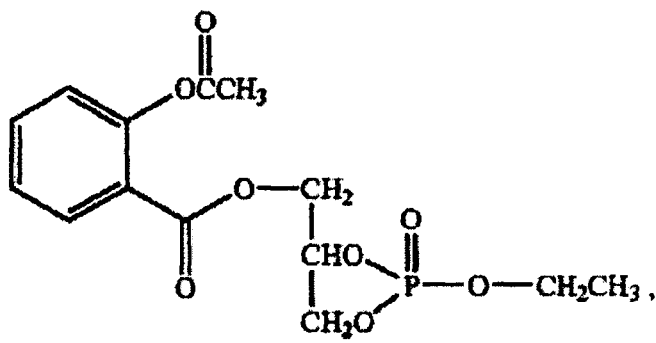
Glycero-phospho-aspirin I
Column 41, line 35, claim 1, the structure:
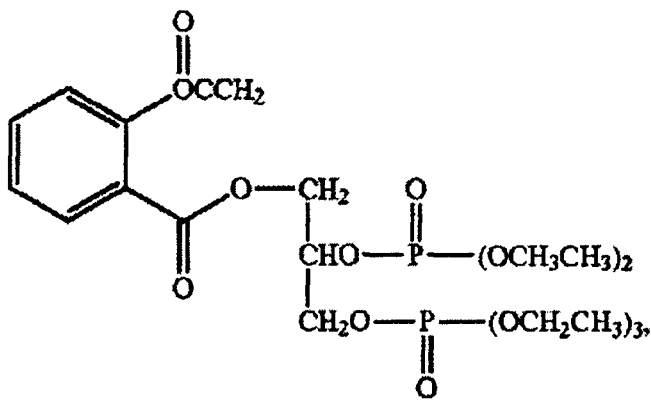
" Glycero-phospho-aspirin II "
should be replaced by the following structure:

CERTIFICATE OF CORRECTION (continued)
U.S. Pat. No. 8,236,820 B2

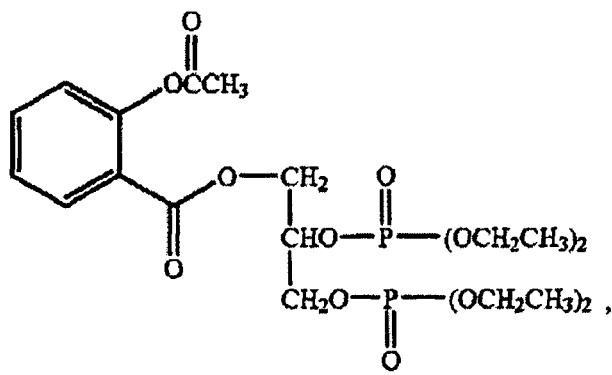

Glycero-phospho-aspirin II

Column 41, line 45, claim 1, the structure:

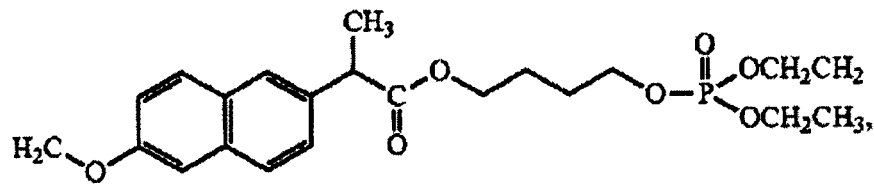

" Phospho-naproxen "

should be replaced by the following structure:

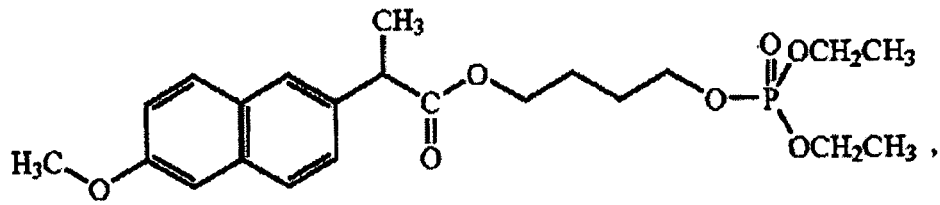

Phospho-naproxen